(12) United States Patent
Blum et al.

(10) Patent No.: US 7,264,777 B1
(45) Date of Patent: Sep. 4, 2007

(54) MEASUREMENT OF SURFACE AREAS BY POLYVINYLPYRROLIDONE SORPTION

(75) Inventors: Alex E. Blum, Boulder, CO (US); Dennis D. Eberl, Boulder, CO (US)

(73) Assignee: The United States of America as represented by the Secretary of the Interior, Washingon, DC (US)

( * ) Notice: Subject to any disclaimer, the term of this patent is extended or adjusted under 35 U.S.C. 154(b) by 773 days.

(21) Appl. No.: 10/641,590

(22) Filed: Aug. 14, 2003

Related U.S. Application Data

(60) Provisional application No. 60/477,725, filed on Jun. 12, 2003.

(51) Int. Cl.
*G01N 30/96* (2006.01)
(52) U.S. Cl. .................. 422/69; 422/68.1; 436/91; 436/96; 436/106; 436/183
(58) Field of Classification Search ............... 422/68.1, 422/69; 436/25, 27, 91, 96, 106, 183
See application file for complete search history.

(56) References Cited

U.S. PATENT DOCUMENTS

| | | | |
|---|---|---|---|
| 2,716,596 A | 8/1955 | Robertson | 23/230 |
| 2,851,881 A | 9/1958 | Daniel et al. | 73/149 |
| 3,299,713 A * | 1/1967 | Haul et al. | 73/865.5 |
| 3,464,796 A | 9/1969 | Freidlander | 23/230 |
| 3,755,659 A | 8/1973 | Bolhuis | 235/151.3 |
| 3,884,083 A | 5/1975 | Lowell | 73/432 PS |
| 3,915,636 A | 10/1975 | Ford, Jr. et al. | 23/230 R |
| 3,944,390 A | 3/1976 | Lieber | 23/230 R |
| 4,495,292 A * | 1/1985 | Siebert et al. | 436/25 |
| 5,578,505 A | 11/1996 | Nuttal et al. | 437/8 |
| 5,825,668 A | 10/1998 | Nakao | 364/564 |
| 6,037,180 A | 3/2000 | Yorkgitis et al. | 436/56 |

OTHER PUBLICATIONS

Pattanaik et al. Materials Letters, vol. 44, 2000, pp. 352-360.*
Sequaris et al. Colloids and Surfaces A: Physicochemical and Engineering Aspects, vol. 159, 1999, pp. 503-512.*
Aylmore L. A. G. and Quirk, J. P. (1967) The micropore size distributions of clay mineral systems. J. Soil Sci., 18:1-17.
Barnett, K. G., Cosgrove, T., Vincent, B. and Sissons, D. S. (1981) Measurement of the polymerbound fraction at the solid-liquid interface by pulsed nuclear magnetic resonance. Macromolecules, 1981:1018-1020.
Blum, Alex E. (1994) Determination of Illite/Smectite Particle Morphology using Scanning Force Microscopy. (in: Scanning Probe Microscopy of Clay Minerals, K. Nagy and A. Blum eds.) Clay Min. Soc., 171-202.
Blum, Alex E. and Eberl, Dennis D. (1992) Determination of clay particle thicknesses and morphology using Scanning Force Microscopy. Proc. 7th International Symp. Water- Rock Interaction, Park City, Utah. A.A. Balkema, Rotterdam, pp. 133-136.

Choiu, Cary T; Rutherford, David W (1997) Effects of exchanged cation and layer charge on the sorption of water and EGME vapors on montmorillonite clays. Clays and Clay Minerals, 45:867-880.
Cohen Stuart, M. A., Fleer, G. J., and Scheutjens, J. M. H. M. (1984) Displacement of polymers. II. Experiment. Determination of segmental sorption energy of poly(vinylpyrrolidone) on silica. J. Colloid and Interface Sci., 97:526-535.
Drits, V.A.; Eberl, D D Srodoñ, (Jan. 1998) XRD measurment of mean thickness, thickness distribution and strain for illite and illite-smectite crystallites by the Bertaut-Warren-Averbach technique. Clays and Clay Minerals, 46:38-50.
Eberl, D D; Drits, V A; Srodoñ, J; Nueesch, R (1996) MUDMASTER; a program for calculating crystallite size distributions and strain from the shapes of X-ray diffraction peaks. U. S. Geol. Sur. Report, OF 96-0171.
Eberl, D.D.; Nüesch, R; Sucha, V; Tsipursky, S (1998) Measurement of fundamental illite particle thicknesses by X-ray diffraction using PVP-10 intercalation. Clays and Clay Minerals, 46: 89-97.
Esmui, K., Takaku, Y. and Otsuka, H. (1994) Introduction between aerosol OT and poly(vinylpyrrolidone) on alumina. Langmuir, 10:3250-3254.
Esmui, K., Iitaka, M. and Torigoe, K. (2000) Kinetics of simultaneous sorption of poly(vinylpyrrolidone)and sodium dodecyl sulfate on alumina particles. J. Colloid and Interface Sci., 232:71-75.
Esumi, Kunio and Oyama, Michiyo (1993) Simultaneous sorption of poly(vinylpyrrolidone) and cationic sufactant from their mixed solutions on silica. Langmuir, 9:2020-2023.
Frances, C. W. (1973) Sorption of polyvinylpyrrolidone on reference clay minerals. Soil Sci., 115:40-54.
Gargallo, L., Pérez-Cotapos, J., Santos, J. G. and Radic D. (1993) Poly(N-vinyl-2-pyrrolidone)-monoalkyl xanthates. 1. Sorption and chemical reaction. Langmuir;681-684.
Gultek, A., Seckin, T., Onal, Y., and Ickuygu, M. G. (2001) Preparation and phenol captivating properties of polyvinylpyrrolidone-montmorillonite hybrid materials. J. Appl. Polymer Sci., 81:512-519.
Gun'ko, V. M., Zarko, E. F., Voroin, E. F., Turov, V. V., Mironyuk, I. F., Gerashchenko, I. I., Goncharuk, E. V. Pakholv, E. M., Guzenko, N. V., Leboda, R., Skubiszewska-Zieba, J., Janusz, W., Chibowski, S., Levchunk, Yu. N., and Klyueva, A. V. (2002) Impact of some organics on structural and sorptive characteristics of furned silica in different media. Langmuir, 18:581-596.
Haung, C. P. and Stumm, W. (1973) Specific sorption of cations on hydrous γ-A1203. J. Colloid Interface Sci., 22:231-259.
Israel, L., Güler, C., Yilmaz, H., and Güler, S. (2001) The sorption of polyvinylpyrrolidone on kaolinite with sodium chloride., J. Colloid and Interface Sci., 238:80-84.
Levy, R. and Francis, C.W. (1975a) Interlayer sorption of polyvinylpyrrolidone on montmorillonite.J. Colloid Interface Sci., 50:442-450.

(Continued)

Primary Examiner—Maureen M. Wallenhorst
(74) Attorney, Agent, or Firm—Mark Homer; Joan Gilsdorf

(57) ABSTRACT

A method of quantitatively determining surface area of a sample uses polyvinylpyrrolidone (PVP) dispersed in a solution containing the sample, and determining the amount of PVP that has deposited on the sample.

15 Claims, 12 Drawing Sheets

OTHER PUBLICATIONS

Levy, R. and Francis, C.W. (1975b) A quantitative method for the determination of montmorillonite in soils. Clays and Clay Min., 23:85-89.

May, H M, Kinniburgh, D G; Helmke, P A, and Jackson, M L (1986) Aqueous dissolution, solubilities and thermodynamic stabilities of common aluminosilicate clay minerals; kaolinite and smectites. Geochim. Cosmochim. Acta, 50:1667-1677.

Misselyn-Bauduin, A., Thibaut, A. Grandjean, J, Broze, G. and Jérôme, R. (2001) Investigation of the interactions of polyvinylpyrrolidone with mixtures of anionic and nonionic surfactants or anionic and zwitterionic surfactant by pulsed field gradient NMR., J. Colloid and Interface Sci., 238:1-7.

Nadeau, P.H. (1985) The physical dimensions of fundamental clay particles. Clay Minerals, 20:499-514.

Nadeau, P.H.; Wilson, M.J.; McHardy, W. J.; Tait, J. M. (1984) Interstratified clays as fundamental particles. Science. 225:923-925.

Otsuka, H. and Esumi, K. (1994) Simultaneous sorption of poly(vinylpyrrolidone) and anionic hydrocarbon/fluorocarbon surfactant from their binary mixtures on alumina: Langmuir, 10:45-50.

Roviro-Bru, M., Giralt, F. and Cohen, Y. (2001) Protein sorption onto zirconia modified with terminally grafted polyvinylpyrrolidone. , J. Colloid and Interface Sci., 235:70-79.

Rutherford, David W; Chiou, Cary T; Eberl, Dennis D (1997) Effects of exchanged cation on the microporosity of montmorillonite. Clays and Clay Minerals, 45:534-543.

Séquaris, J. -M., Decimavilla, S. Camara and Ortega, J. A. Corrales (2002) Polyvinylpyrrolidone sorption and structural studies on homoioic Li-, Na- K- and Cs-montmorillonite colloidal suspensions. J. Colloid and Interface Sci., 252:93-101.

Séquaris, J. -M., Hind A., Narres, H. D. and Schwuger, M. J. (2000) Polyvinylpyrrolidone sorption on Na-montmorillonite. Effect of the polymer interfacial conformation on the behavior and binding of chemicals. J. Colloid and Interface Sci., 230:73-83.

Smith, J. N., Meadows, J. and Williams, P. A. (1996) Sorption of polyvinylpyrrolidone onto polystyrene lattices and the effect on colloid stability. Langmuir, 12:3773-3778.

Srodoñ, J; Eberl, D D; Drits, V A (2000) Evolution of fundamental-particle size during illitization of smectite and implications for reaction mechanism. Clays and Clay Minerals, 48:446-458.

Srodoñ, Jan, Drits, Victor A, McCarty, Douglas K, Hsieh, Jean C C, and Eberl, Dennis D (2001) Quantitative x-ray diffraction analysis of clay-bearing rocks from random preparations. Clays and Clay Min. 49:514-528.

Srodon, J., Morgan, D. J., Eslinger, E. V., Eberl, D. D., and Karlinger, M. R., 1986, Chemistry of illite/smectite and end-member illite: Clays and Minerals, v. 34, p. 268-378.

Sun, T and King, H.E. (1996) Aggregation behavior in the semidulute poly(N-vinyl-2- pyrrolidone)/water system. Macromolecules, 29:3175-3181.

Thibaut, A., Misselyn-Bauduin, A. M. Broze, G. and Jérôme, R. (2000) Sorption of poly(vinylpyrrolidone)/Surfactant(s) mixtures at the silica/water interface. Langmuir, 16:9841-9849.

Uhlik, P., Šucha, V., Elsass, F., and Caplovicova, M. (2000) High-resolution transmission electron microscopy of mixed-layer clays dispersed in PVP-10; A new technique to distinguish detrital and authigenic illitic material. Clay Min., 35:781-789.

* cited by examiner

MEASUREMENT OF SURFACE AREAS BY POLYVINYLPYRROLIDONE SORPTION

STATEMENT REGARDING PRIORITY DATE

This application is based upon provisional application 60/477,725, filed on Jun. 12, 2003 and this priority date is hereby claimed for this application.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

1. Field of the Invention

The present invention provides a determination of surface areas by measurement of polyvinylpyrrolidone adsorption in solution.

2. Brief Description of the Related Art

Smectitic minerals may have a dramatic, sometimes dominate, effect on the physical and chemical properties of soils and sediments because of their high surface areas, high cation exchange capacities and swelling properties. However, the quantification of smectite minerals in sediments has remained problematic (see e.g., Srödon, Jan, Drits, Victor A, McCarty, Douglas K, Hsieh, Jean C C, and Eberl, Dennis D (2001) Quantitative x-ray diffraction analysis of clay-bearing rocks from random preparations. Clays and Clay Min. 49:514-528). The fundamental question of "what is a smectite?" has been a popular philosophical topic among clay mineralogists. A traditional mineralogic definition, based on the mineral chemistry and structure, is difficult to apply both because of the wide range of possible compositions, and because of the practical difficulty of isolating any single pure clay phase from a mixture for accurate chemical analysis. In fact, compositional variability between and within individual smectite particles may mean that smectitic minerals actually defy the strict definition of a phase (see e.g., May, H M, Kinniburgh, D G; Helmke, P A, and Jackson, M L (1986) Aqueous dissolution, solubilities and thermodynamic stabilities of common aluminosilicate clay minerals; kaolinite and smectites. Geochim. Cosmochim. Acta, 50:1667-1677). Before the work of Nadeau (Nadeau, P. H. (1985) The physical dimensions of fundamental clay particles. Clay Minerals, 20:499-514; and Nadeau, P. H.; Wilson, M. J.; McHardy, W. J.; Tait, J. M. (1984) Interstratified clays as fundamental particles. Science. 225:923-925. 1984, 1985) and others, a practical working definition of smectites was any clay that swells to 17 Å when exposed to ethylene glycol vapor. However, this functional definition has become increasingly problematic as additional work has shown that illite-smectite mixed layer clays can be dispersed into fundamental particles. When in a dispersed state, the illite particles display only a 10 Å XRD peak (see e.g., Eberl, D. D.; Nüesch, R; Sucha, V; Tsipursky, S (1998) Measurement of fundamental illite particle thicknesses by X-ray diffraction using PVP-10 intercalation. Clays and Clay Minerals, 46: 89-97). However, when dried, the interfaces between the reassembled illite particles can be X-ray coherent, and yield layers that expand to 17 Å in ethylene glycol. Thus, a sample of "pure illite" particles can produce the characteristic smectite swelling with glycolation, even though strictly speaking, no smectite is present. A more accurate working definition of a smectite is a 2:1 clay which, when Na saturated, can be dispersed as a single unit cell thick particle in aqueous solution, which is the presently used concept of a smectite.

Traditional measurements of surface areas on dried samples may not accurately reflect the surface areas of material in suspension. For example, smectite particles can be dispersed in solution as single unit cell (~1 nm) thick particles, and this is the surface area which controls the physical and chemical properties of smectites. However, when smectites are dried, they form XRD coherent aggregates, making the interfaces between the particles inaccessible to most traditional measures of surface area, such as $N_2$ adsorption (BET), which must be performed on solid samples.

X-ray diffraction (XRD) has been found to be an inappropriate method for quantifying these smectite particles. Completely dispersed smectite particles have no (001) XRD peak, because a single unit cell does not have a repeat distance in the c direction (see e.g., Eberl et al., 1998, identified above). The a-b plane of smectites generate XRD peaks (particularly the (060)), but these peaks closely overlap with illites and micas, which are nearly ubiquitous in natural samples. When smectites and illites are dried, the particles are easily deformed by strong surface interactions to form highly oriented and coherent aggregates of illite/smectite crystals (see e.g., Blum, Alex E. (1994) Determination of Illite/Smectite Particle Morphology using Scanning Force Microscopy. (in: Scanning Probe Microscopy of Clay Minerals, K. Nagy and A. Blum eds.) Clay Min. Soc., 171-202) which generate the commonly observed (001) diffraction peaks by interparticle diffraction (see e.g., Nadeau, et al., 1984, identified above). However, in complex mixtures containing minerals in addition to smectite, both the "stacking" efficiency and the crystal orientation relative to the X-ray beam become highly variable, making quantification of smectites using the (001) XRD peaks inaccurate.

During sorption of inert gases in a dry environment, (e.g., using $N_2$, Kr or various organic vapors by the Brunnuer, Emmet and Teller (BET) method) the gas does not access the "internal" surfaces between coherently stacked crystals, and therefore, grossly underestimates the smectite surface area that is exposed to solution (see e.g., Aylmore L. A. G. and Quirk, J. P. (1967) The micropore size distributions of clay mineral systems. J. Soil Sci., 18:1-17). Smectites also may be quantified by measurement of the cation exchange capacity (CEC). However, the CEC of smectites can vary by almost a factor of two, leading to a similar error in using cation exchange capacity to quantify smectite abundance. In addition, other minerals and organic matter may also contribute to the CEC in an unquantifiable manner.

Although the sorption of ethylene glycol monoethyl ether (EGME) has been suggested as a technique to quantify smectite abundance, recent works (see e.g., Chiou, Cary T; Rutherford, David W (1997) Effects of exchanged cation and layer charge on the sorption of water and EGME vapors on montmorillonite clays. Clays and Clay Minerals, 45:867-880; and Rutherford, David W; Chiou, Cary T; Eberl, Dennis D (1997) Effects of exchanged cation on the microporosity of montmorillonite. Clays and Clay Minerals, 45:534-543) has shown that sorption of EGME is highly dependent on the EGME partial pressure, exchangeable cation and layer charge as well as void sizes and organic carbon content.

Polyvinylpyrrolidone (PVP, CA#9003-39-8) is a widely used industrial surfactant, emulsifier and adhesive, with applications including hair spray, textile dye stripping, extender for blood plasma, ink-jet printing, tablet binder in pharmaceuticals, and the adhesive at both ends of toilet paper rolls. PVP polymers are synthesized from monomer units. PVP is available in a variety of chain lengths with molecular weights (MW) ranging from 10K to 1200K, which corresponds to chains of about 90 to 11,000 monomers.

PVP has been widely investigated as a surfactant (see e.g., Frances, C. W. (1973) Sorption of polyvinylpyrrolidone on reference clay minerals. Soil Sci., 115:40-54). Levy and Frances (Levy, R. and Francis, C. W. (1975a) Interlayer sorption of polyvinylpyrrolidone on montmorillonite. J. Colloid Interface Sci., 50:442-450) first studied the sorption behavior of PVP on montmorillonites, and Levy and Frances (Levy, R. and Francis, C. W. (1975b) A quantitative method for the determination of montmorillonite in soils. Clays and Clay Min., 23:85-89) proposed using a XRD technique utilizing intercalated PVP to quantify the amount of montmorillonite in a sample in the presence of other swelling clays, such as vermiculite. The nature of PVP binding to montmorillonite surfaces has also been studied (see e.g., Gultek, A., Seckin, T., Onal, Y., and Ickuygu, M. G. (2001) Preparation and phenol captivating properties of polyvinylpyrrolidone-montmorillonite hybrid materials. J. Appl. Polymer Sci., 81:512-519; Séquaris, J. B M., Decimavilla, S. Camara and Ortega, J. A. Corrales (2002) Polyvinylpyrrolidone sorption and structural studies on homoioic Li-, Na- K- and Cs-montmorillonite colloidal suspensions. J. Colloid and Interface Sci., 252:93-101; and Séquaris, J. B M., Hind A., Narres, H. D. and Schwuger, M. J. (2000) Polyvinylpyrrolidone sorption on Na-montmorillonite. Effect of the polymer interfacial conformation on the behavior and binding of chemicals. J. Colloid and Interface Sci., 230:73-83). There have been studies of PVP sorption on silica (see e.g., Cohen Stuart, M. A., Fleer, G. J., and Scheutjens, J. M. H. M. (1984) Displacement of polymers. II. Experiment. Determination of segmental sorption energy of poly(vinylpyrrolidone) on silica. J. Colloid and Interface Sci., 97:526-535; Esumi, Kunio and Oyama, Michiyo (1993) Simultaneous sorption of poly(vinylpyrrolidone) and cationic surfactant from their mixed solutions on silica. Langmuir, 9:2020-2023; Gun=ko, V. M., Zarko, E. F., Voroin, E. F., Turov, V. V., Mironyuk, I. F., Gerashchenko, I. I., Goncharuk, E. V. Pakhlov, E. M., Guzenko, N. V., Leboda, R., Skubiszewska-Zieba, J., Janusz, W., Chibowski, S., Levchunk, Yu. N., and Klyueva, A. V. (2002) Impact of some organics on structural and sorptive characteristics of fumed silica in different media. Langmuir, 18:581-596; and Thibaut, A., Misselyn-Bauduin, A. M., Broze, G. and Jérôme, R. (2000) Sorption of poly(vinylpyrrolidone)/Surfactant(s) mixtures at the silica/water interface. Langmuir, 16:9841-9849), on alumina (see e.g., Otsuka, H. and Esumi, K. (1994) Simultaneous sorption of poly(vinylpyrrolidone) and anionic hydrocarbon/fluorocarbon surfactant from their binary mixtures on alumina. Langmuir, 10:45-50; Esmui, K., Takaku, Y. and Otsuka, H. (1994) Introduction between aerosol OT and poly(vinylpyrrolidone) on alumina. Langmuir, 10:3250-3254; and Esmui, K., Iitaka, M. and Torigoe, K. (2000) Kinetics of simultaneous sorption of poly(vinylpyrrolidone) and sodium dodecyl sulfate on alumina particles. J. Colloid and Interface Sci., 232:71-75), on kaolinite (see e.g., Israel, L., Güler, C., Yilmaz, H., and Güler, S. (2001) The sorption of polyvinylpyrrolidone on kaolinite with sodium chloride., J. Colloid and Interface Sci., 238:80-84), and on zirconium (see e.g., Rovira-Bru, M., Giralt, F. and Cohen, Y. (2001) Protein sorption onto zirconia modified with terminally grafted polyvinylpyrrolidone., J. Colloid and Interface Sci., 235:70-79). There have also been more general studies of the binding configuration and structure of PVP both on surfaces and in solution (see e.g., Barnett, K. G., Cosgrove, T., Vincent, B. and Sissons, D. S. (1981) Measurement of the polymerbound fraction at the solid-liquid interface by pulsed nuclear magnetic resonance. Macromolecules, 1981:1018-1020; Gargallo, L., Pérez-Cotapos, J., Santos, J. G. and Radic D. (1993) Poly(N-vinyl-2-pyrrolidone)-monoalkyl xanthates. 1. Sorption and chemical reaction. Langmuir; 681-684; Misselyn-Bauduin, A., Thibaut, A. Grandjean, J, Broze, G. and Jérôme, R. (2001) Investigation of the interactions of polyvinylpyrrolidone with mixtures of anionic and nonionic surfactants or anionic and zwitterionic surfactant by pulsed field gradient NMR., J. Colloid and Interface Sci., 238:1-7; Smith, J. N., Meadows, J. and Williams, P. A. (1996) Sorption of polyvinylpyrrolidone onto polystyrene lattices and the effect on colloid stability. Langmuir, 12:3773-3778; and Sun, T and King, H. E. (1996) Aggregation behavior in the semidilute poly(N-vinyl-2-pyrrolidone)/water system. Macromolecules, 29:3175-3181). Most of these studies were broadly aimed at understanding how PVP sorption can be used to modify colloid particle surfaces for better dispersion during industrial applications. Additionally, PVP 10K has been used to intercalate illite fundamental particles for XRD analysis (Eberl, D D; Drits, V A; Srodoñ, J; Nueesch, R (1996) MUDMASTER; a program for calculating crystallite size distributions and strain from the shapes of X-ray diffraction peaks. U.S. Geol. Sur. Report, OF 96-0171; Eberl et al., 1998, identified above; and Uhlik, P., Sucha, V., Elsass, F., and Caplovicova, M. (2000) High-resolution transmission electron microscopy of mixed-layer clays dispersed in PVP-10; A new technique to distinguish detrital and authigenic illitic material. Clay Min., 35:781-789), such that when the PVP/clay suspension is evaporated, the PVP widely separates the illite particles, eliminating interparticle diffraction, and allowing the quantification of illite particle thicknesses from the broadening of the (001) peak.

There is a need in the art for improvements in the measurement of the surface area of smectite crystals. The present invention addresses this and other needs.

SUMMARY OF THE INVENTION

The present invention includes a method of quantitatively determining surface area of a sample that includes the steps of selecting a solution, dispersing a sample in the solution, and adding polyvinylpyrrolidone in the solution, wherein the polyvinylpyrrolidone deposits on the surface of the sample, removing at least a portion of the solution having the added polyvinylpyrrolidone that has not deposited on the dispersed sample, quantifying the mass of the added polyvinylpyrrolidone, that has not deposited on the dispersed sample, from the removed at least a portion of the solution, determining the loss of polyvinylpyrrolidone from the solution from the quantified mass of added polyvinylpyrrolidone and determining the mass of the polyvinylpyrrolidone deposited on the surface area of the sample from the determined loss of polyvinylpyrrolidone from the solution. In addition to the method above, the present invention also may include the step of calculating the surface area of the sample from the determined mass of the polyvinylpyrrolidone deposited on the surface area of the sample. Additionally, the present invention also may include the step of calculating the content of a smectite, illite, kaolinite and chlorite sample from the calculated surface area of the sample.

Furthermore, the present invention includes the determined surface area product of method, above, including determined smectite or illite surface area products.

The present invention avoids the difficulty of measuring the surface area of a sample by measuring adsorption of PVP in solution, when all the external surfaces of the sample, preferably smectite crystals, are exposed.

DETAILED DESCRIPTION OF THE PREFERRED EMBODIMENT

Figure 1:
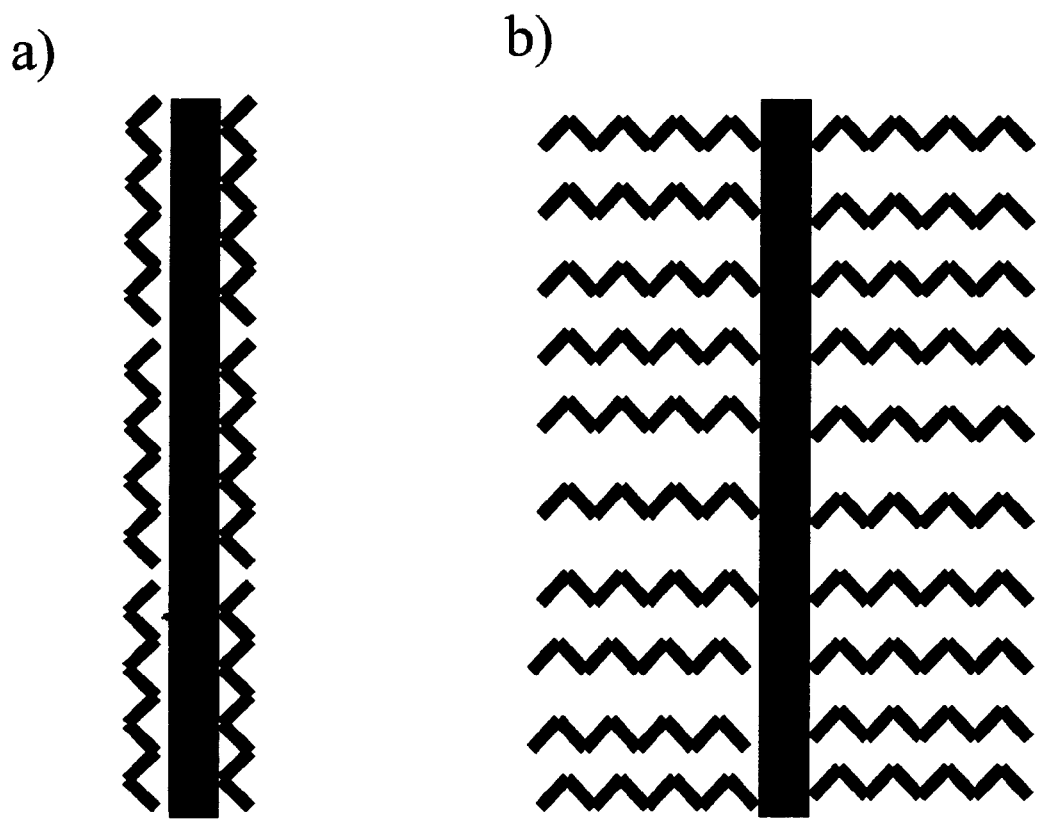
FIG. 1(a) illustrates that planar faces of smectite particles in dried samples have strong attractive forces with most silicate minerals, which easily deform the crystals to the underlying surface, by illustrating a high degree of smectite conformation and orientation in samples with high smectite contents.
FIG. 1(b) illustrates that planar faces of smectite particles in dried samples have strong attractive forces with most silicate minerals, which easily deform the crystals to the underlying surface, by illustrating that a lower and variable degree of coherent smectite stacking and orientation occurs in mixtures containing other minerals in addition to smectites.

The present invention provides a measurement of surface areas for fine grained material, particularly clay surface areas such as smectite, illite, kaloinite, chlorite and combinations thereof, by polyvinylpyrrolidone (PVP) sorption. As such, the present invention also provides a useful new method for quantifying the abundance of the clay, particularly smectite, illite, kaolinite, chlorite and combinations thereof.

The method of the present invention quantitatively determines surface area of the sample by calculating the transfer of PVP from a solution onto the sample. As detailed herein, the method includes the steps of selecting a solution, dispersing a sample in the solution, adding polyvinylpyrrolidone in the solution, wherein the polyvinylpyrrolidone deposits on the surface of the sample, removing at least a portion of the solution having the added polyvinylpyrrolidone that has not deposited on the dispersed sample and determining the mass of the polyvinylpyrrolidone deposited on the surface area of the sample from the transfer of polyvinylpyrrolidone from the solution to the surface of the sample.

The method of the present invention includes selection of an appropriate solution. Useful solutions for the present invention include any appropriate solution for dispersal of the sample, and polyvinylpyrrolidone to attach thereto. Representative examples of the solution include without limitation water, one or more organic solvents and combinations thereof. Preferably the solution includes water.

Preferably, the step of dispersing the sample in the solution includes saturating the samples sample's exchange sites with sodium or lithium ions. Salts of the sodium or lithium may then be removed from the sample prior to adding polyvinylpyrrolidone in the solution. The step of dispersing the sample in the solution may include any appropriate means of dispersal to distribute, divide, partition, or otherwise disseminate the sample into the solution. Representative dispersal means include for example without limitation stirring, shaking, ultrasonic agitation, and combinations thereof, with selection of the dispersal means determinable by one skilled in the art.

Addition of PVP into solution includes an appropriate amount of PVP, detailed herein, to coat the sample of surface area determination. Such amounts of PVP include for example, 2 ml of solution that is 10% by weight PVP per 50 mg of pure smectite, and the like.

A portion of the solution containing the PVP is removed to determine the amount of PVP that has deposited onto the sample. The portion of sample may include for example, from about 2 mL to about 4 mL, or other appropriate amounts to determine the PVP concentration remaining in solution.

The sample, having the deposited polyvinylpyrrolidone thereto, may be concentrated prior to removing all or part of the solution. Concentration of the sample includes any appropriate concentrating means such as, for example without limitation, centrifugation, flocculation, dialysis and other like known concentrating means including combinations thereof. In one preferred embodiment, the step of concentrating the sample comprises centrifugation.

Determination of the mass of the polyvinylpyrrolidone deposited on the surface area of the sample from the transfer of polyvinylpyrrolidone from the solution to the surface of the sample may include such steps as calculating the surface area of the sample from the determined mass of the polyvinylpyrrolidone deposited on the surface area of the sample, quantifying the mass of the added polyvinylpyrrolidone, that has not deposited on the dispersed sample, from the removed at least a portion of the solution, determining the loss of polyvinylpyrrolidone from the solution from the quantified mass of added polyvinylpyrrolidone, determining the mass of the polyvinylpyrrolidone deposited on the surface area of the sample from the determined loss of polyvinylpyrrolidone from the solution and the like.

Smectite particles can be dispersed as single unit cell thick (~1 nm) particles in solution. It is the surface area of these particles that is most accessible to solution, and which controls the physical and chemical properties of smectites in saturated environments.

The present invention provides a determined surface area of the sample because of the uniform adherence of the PVP to the sample. FIGS. 1(a) and 1(b) illustrate that the planar faces of smectite particles in dried samples have strong attractive forces with most silicate minerals, which easily deform the crystals to the underlying surface. As illustrated in FIG. 1(a), there exists a high degree of smectite conformation and orientation in samples with high smectite contents, whereas, as shown in illustration FIG. 1(b), a lower and variable degree of coherent smectite stacking and orientation occurs in mixtures containing other minerals in addition to smectites.

Figure 2:
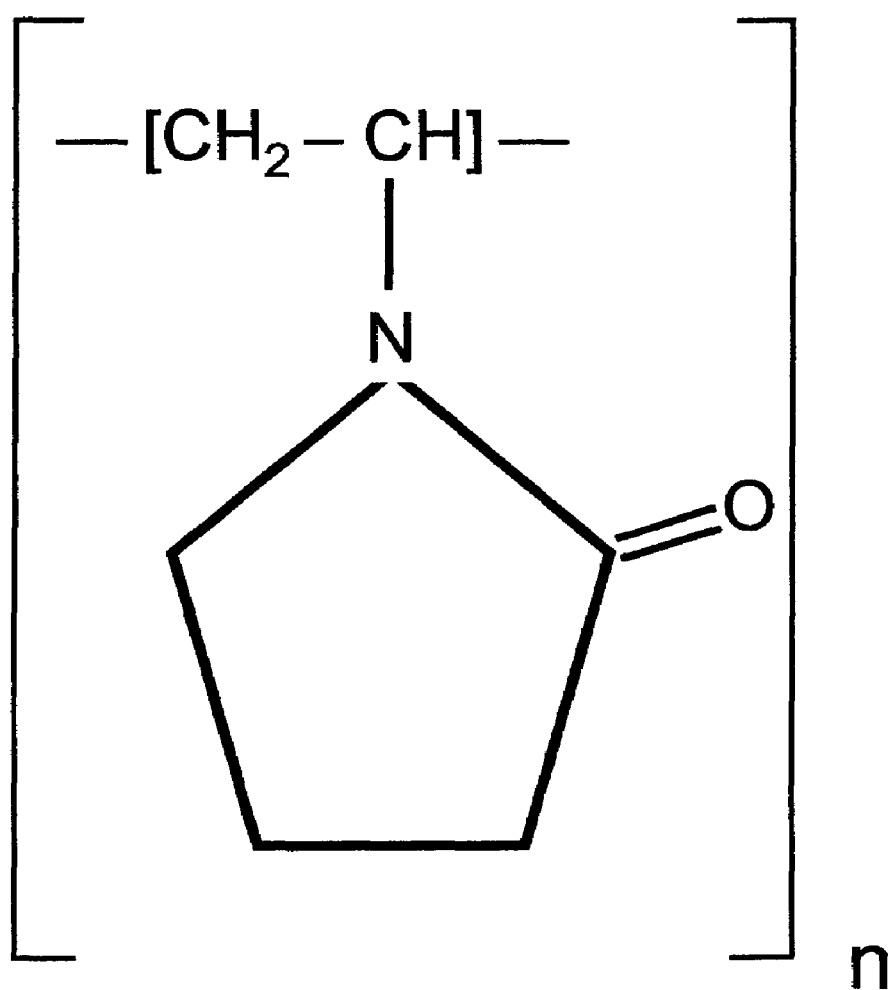
FIG. 2 represents the chemical structure of polyvinylpyrrolidone (PVP)

The method and quantitative product determine smectite abundance using polyvinylpyrrolidone (PVP), having a chemical structure as shown in FIG. 2, from PVP sorption on smectite particles dispersed in aqueous solution containing a known concentration of PVP. Sorption density of PVP-55K on a wide range of smectites, illites and kaolinites is approximately 0.99 mg/m$^2$, which corresponds to approximately 0.72 g of PVP-55K per gram of montmorillonite. PVP sorption on smectites is generally independent of layer charge and solution pH. PVP sorption on $SiO_2$, $Fe_2O_3$ and ZnO normalized to the BET surface area are similar to the sorption densities on smectites. $\gamma$-$Al_2O_3$, amorphous $Al(OH)_3$ and gibbsite all show no PVP sorption over a wide range of pH, and sorption of PVP by organics is minimal. The insensitivity of PVP sorption densities to mineral layer charge, solution pH and mineral surface charge suggests that PVP sorption is not localized at charged sites, but is controlled by more broadly distributed interactions such as Van der Waal's interactions and/or hydrogen bonding. Smectites have very high surface areas when dispersed as single unit cell thick particles, approximately 725 m$^2$/g, and usually dominate the total surface areas of natural samples in which smectites are present. Accordingly, in the present case, smectite abundance is directly proportional to PVP sorption. In other cases, however, the accurate quantification of smectite abundance by PVP sorption may require minor corrections for PVP uptake by other phases, principally illite and kaolinite. Quantitative XRD can be combined with PVP uptake measurements to uniquely determine the smectite concentration in such samples.

Within the process of the present invention, the amount of sample that can be used may be varied, which may be limited particularly with regard to the suspending a large amount of surface area for low surface area material, e.g., difficultly may exist in effectively suspending 40 m$^2$ of surface area when analyzing low surface area (<50 m$^2$/g) samples such as kaolinite or silica. Preferably a limit of a sample size of 1 g per 5 ml water is used for fine material (<2 µm), but larger masses of high silt or sand samples can be accommodated. The amount of PVP solution added can be adjusted for low or high surface area samples effective to maintain a nearly constant final PVP concentration in solution. This precaution retains sensitivity in the analysis while remaining on the flat portion of the sorption isotherm. For example, the Wyoming and Belle Fourche low-charge smectites and the RM30 illite were measured with both immediate centrifugation and overnight shaking after the addition of PVP. Samples with immediate centrifugation sorbed >90% of the PVP sorbed overnight, showing the PVP sorption kinetics as fast. However, sorption kinetics was not investigated for a wide spectrum of materials, and samples were routinely shaken overnight to assure complete sorption.

Settling of single unit cell thick smectite particles is difficult, and requires considerable centrifugation. However, PVP sorbed on the clay surfaces prevents flocculation by traditional techniques such as adding methanol, acetone, increasing ionic strength or manipulating solution pH. As a result, high speed centrifugation was used to remove the clays from solution. Although some small clay particles remain suspended in solution, the error introduced by these suspended clay particles is proportional to the fraction of clay remaining in solution. Through experimentation of using different centrifuge times, including up to 48 hrs, errors introduced by any incomplete settling of a few fine particles remained at less than 1% of the PVP sorbed as long as the solutions appeared completely clear to the eye. Gravimetric analysis is preferred over (the simpler method of) UV sorption to measure the PVP concentrations in solution, as UV sorption spectra is highly influenced by residual colloids in solution. As complete removal of the smectite particles from solution is extremely difficult, the UV analytical method failed to produce reliable and reproducible PVP concentrations for smectite containing samples.

PVP hydration after it is removed from the oven remains problematic such as, for example, gaining several weight percent of water in a time period of from about 5 days or less. PVP hydration can lead to large calculation errors of the mass of PVP sorbed. The rate of PVP weight gain by hydration is initially rapid, decreasing dramatically after about 1 hour, but continuing for days at a slow rate. As such, samples are preferably isolated from the atmosphere, such as with an inert gas of argon or nitrogen, and measurement the mass occurs soon after the vials cool. Preferably polystyrene vials are used, which were experimentally found to occasion a smaller change in mass with heating and cooling than glass or polyethylene vials, and yielded the more reproducible results. Additionally, as complete dehydration of the PVP is desired, the samples are preferably heated in the oven for several additional hours after the samples appear dry.

A. Preparation of PVP Reagent

PVP reagent is prepared in a manner that uniformly disperses the PVP in solution. PVP has a nearly infinite solubility in water, but the dissolution kinetics can be very slow. Typically, approximately 50 g of 55K PVP reagent is dissolved in approximately 400 ml of distilled water. The beaker is usually stirred and gently heated on a hot plate for several hours. PVP of all molecular weights seemed stable up to at least 120 C, and the reported melting point of PVP-55K is >300 C. The solution is then transferred to a volumetric flask, cooled to room temperature, and diluted to 500 ml. The PVP solutions are stable indefinitely if sterile, but are subject to biodegradation. Therefore, solutions were usually refrigerated to retard colonization if they were stored for more than a few days. Each batch of PVP reagent is individually calibrated, typically by evaporating multiple aliquots of about 1 mL to about 10 mL of solution at 85 C as described in Example 1 (A sample vial is weighed with the lid, solution is decanted into the vial, closed and weighed. The beaker is then dried at 85 C overnight, capped immediately after being removed from the oven, and reweighed when cooled). Reproducibility is generally <±0.2%, and yields a final solution between about 9.4 and about 9.5 wt. % PVP, indicating the initial reagent is approximately 5 wt. % water.

B. Determination of Sample Specific Surface Areas

In examining the behavior of PVP sorbed on minerals, and in the development and validation of the PVP sorption method, an independent measure of the mineral surface area is desirable in order to evaluate the sorption density. However, there is no other reliable technique for determination of smectite surface area. Because the geometry of the smectite crystals is known, a theoretical surface area may be calculated. Smectite crystals are about 1 nm thick, and from TEM (Nadeau, 1985, previously identified) and AFM (Blum, 1994, previously identified), the disclosure of which are hereby incorporated by reference, observations they have diameters from about 0.1 to about 2 µm. Using the lower bound of 0.1 µm for the diameter, the edges are calculated to contribute <2% of the surface area. Therefore, smectite may be treated as an infinitely large sheet 1 nm thick for the calculation of surface area. Although the chemistry of smectites may vary greatly, the structure is always very similar to muscovite, and consequently the molar volume ($V_{mol}$) of muscovite (140.71 cm³/mol (Robie, Richard A., Hemingway, Bruce S. and Fisher, James R. (1979) Thermodynamic Properties of Mineral and Related Substances at 298.15 K and 1 Bar Pressure and at higher Temperatures. U.S. Geol. Sur. Bull. 1452., the disclosure of which is hereby incorporated by reference)) may be used as $V_{mol}$ for all smectites. This volume neglects interlayer swelling by hydration, but this is appropriate since the interlayer water in either the chemistry or volume assumptions are consistently not included.

The surface area of a smectite will then be, Equation (1) below:

$$SA = 2V_{mol}/hF_{wt} \quad \text{(eq. 1)}$$

where SA is the specific surface area (defined as surface area/mass), h is the thickness of the crystal (for muscovite and smectites h=1 nm), and $F_{wt}$ is the formula weight of the mineral. For a typical montmorillonite, this formula yields a specific surface area of approximately 755 m²/g. However, this SA is calculated for dehydrated smectite. Montmorillonite which is oven dried at 105 C still retains about 4.0 wt. % interlayer water (determined by heating at 300 C overnight) but the effective SA remains the same. This reduces the specific surface area of a smectite sample weighed in air by about 4%, to approximately 725 m²/g for a typical montmorillonite. Equation (1) is used to calculate the surface areas of many of the smectites shown in Table 1, below.

For pure illite, surface areas also are calculated using Equation (1), except that h is taken as the area weighted mean crystallite thickness determined using the MudMaster program (Eberl et al., 1996, previously identified, the disclosure of which is hereby incorporated by reference), which analyzes XRD peak shapes to determine crystal size distributions. For all the minerals except smectite and illite, the BET surface area was used, measured by sorbing and desorbing $N_2$ from the surface. These samples all have a more blocky morphology without significant coherent stacking and interparticle diffraction. Consequently, it may be assumed that in the dried samples, $N_2$ which has a diameter similar to that of a water molecule, has access to the same surfaces which are accessed by solution after aqueous dispersion.

C. Sorption on Smectites

Figure 3:
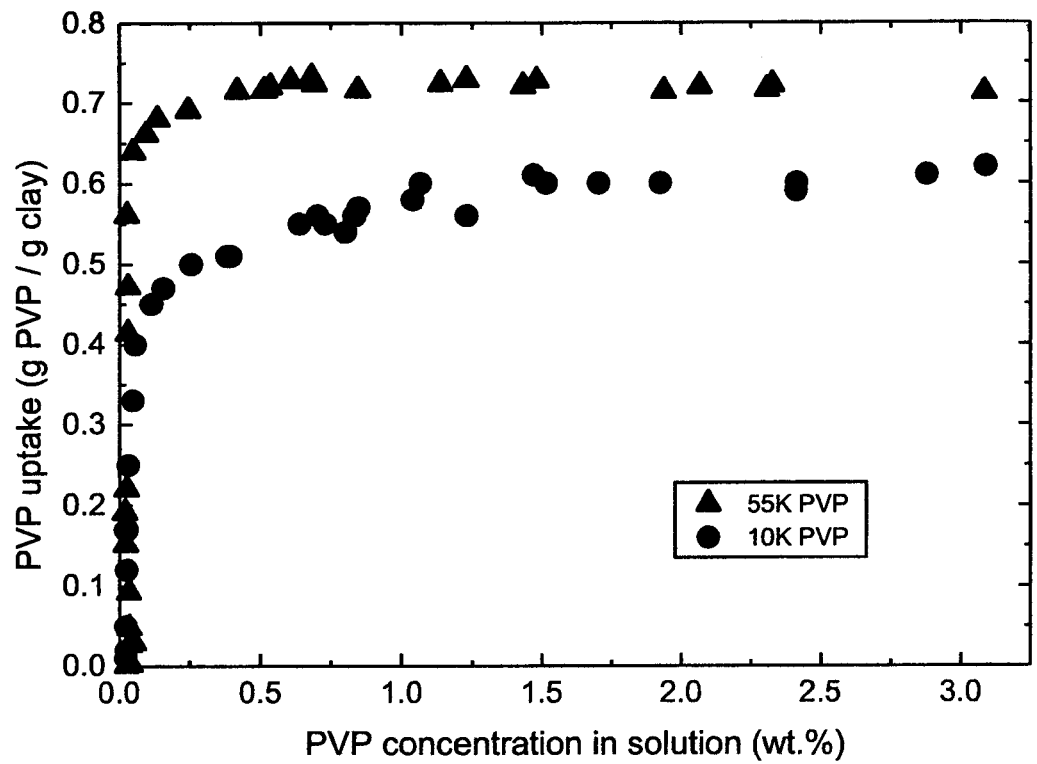
FIG. 3 is a graphical representation of a sorption isotherm of 55K and 10K PVP on Belle Fourche smectite.

A sorption isotherm for the Belle Fourche bentonite (a low charge montmorillonite) is shown in the graphical representation of FIG. 3 for PVP-10K and –55K. The general shape of the isotherms shown in FIG. 3 are consistent with the sorption of PVP on the clay surface, with a well defined surface saturation plateau at 0.61 g and 0.72 g of PVP sorbed per gram of clay (g/g) for PVP-10K and PVP-55K, respectively. The sorption isotherms are not fitted well by either a theoretical Langmuir or Freundlich isotherm, as is evident by the non-linearity of either a reciprocal or log-log plot, respectively (not shown). Nevertheless, there is a wide range of solution PVP concentrations at which the amount of PVP sorption is nearly constant. Throughout this range of solution PVP concentration, the amount of PVP sorbed is proportional to the amount of clay present, but independent of the solution composition.

There is also a trend of slightly greater PVP sorption with increasing polymer chain length, which is observed over a range of PVP molecular weights from 10K (0.61 g/g) to 360K (0.76 g/g). The mass of PVP sorbed per unit mass (or SA) increases only slightly (approximately 20%) as the polymer chain length increases by a factor of 36, indicating that the area per polymer unit (represented in FIG. 2) remains nearly constant. This observation is consistent with a conceptual model in which the PVP chains are lying on the surface, and not analogous to detergents which are arranged perpendicular to the surface.

The unbonded electron pairs on either the amine or the carbonyl groups located on the five member ring of PVP might be expected to act as a weak Lewis bases. However, PVP does not appear to protonate significantly in the near-neutral pH region. A solution of 1% PVP-10K was titrated with HCl and NaOH. The solution neutralized 92 µeq of charge per gram of PVP-10K between pH 5 and pH 9, which corresponds to about 1 charge per polymer chain. In practice, the PVP does not significantly buffer the solution pH. The pH of a 1 wt. % PVP solution is approximately 8.5, but the pH of the final suspension is controlled primarily by the surface chemistry of the sample, which in turn often reflects the last solution to which the sample was exposed.

Figure 4:
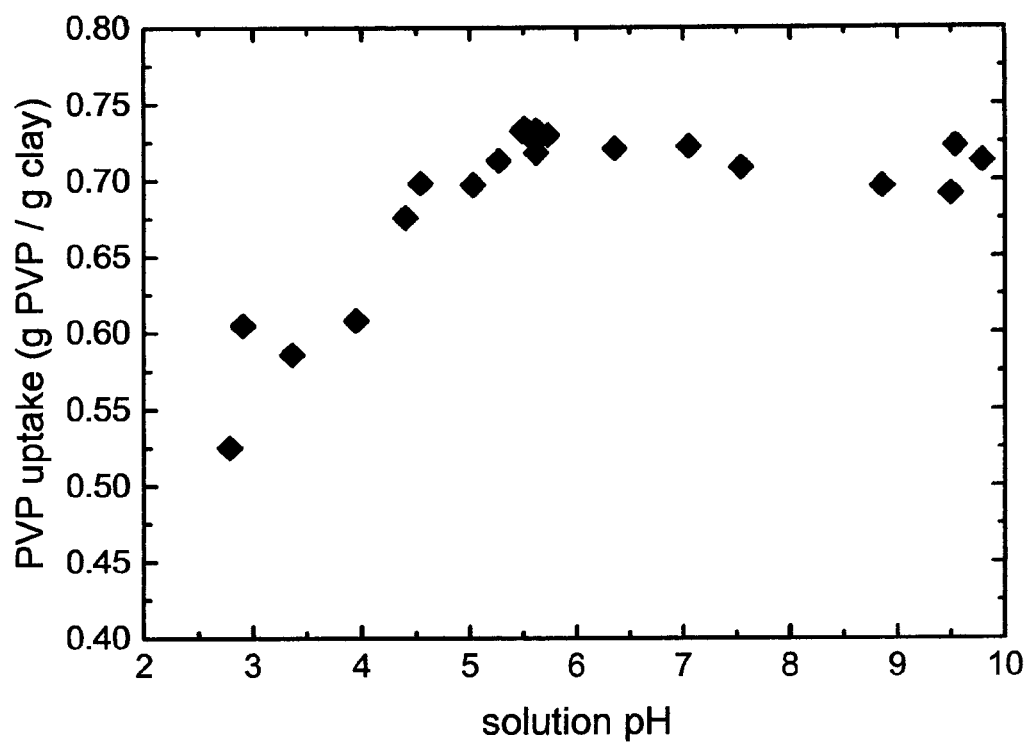
FIG. 4 is a graphical representation of the effect of solution pH on the sorption of PVP on Belle Fourche smectite.

FIG. 4 is a graphical representation of the effect of solution pH on the sorption of PVP on Belle Fourche smectite, and as seen therein, shifting the solution pH (by the addition of $NH_4OH$ or HCl, which should be lost in the vapor phase when evaporated) had no discernible effect on the amount of PVP sorbed on smectites, at least in the pH range from 6 to 10. There does appear to be some effect of low pH on PVP sorption, but this is believed to be an experimental artifact. As hydrochloric acid is added to the suspension, protons substitute for $Na^+$ on the smectite exchange sites, releasing $Na^+$ to solution. When the solution is evaporated, the $Na^+$ is retained as NaCl. This gives the appearance of a greater mass of PVP in solution, and therefore less PVP is calculated as sorbed on the clay. Differences in the fixed charge of the smectite, shown in Table 1 below, also had no discernible effect on the PVP sorption density in the range from 0.3 to 0.8 charges per half formula unit, nor does it appear to be affected by whether or not the charge is in tetrahedral or octahedral layers. This is particularly evident by the similar PVP uptake of the Wyoming and Belle Fourche low-charge smectites, and the Cheto, Kinney and Outay high-charge smectites (see Table 1).

Figure 5:
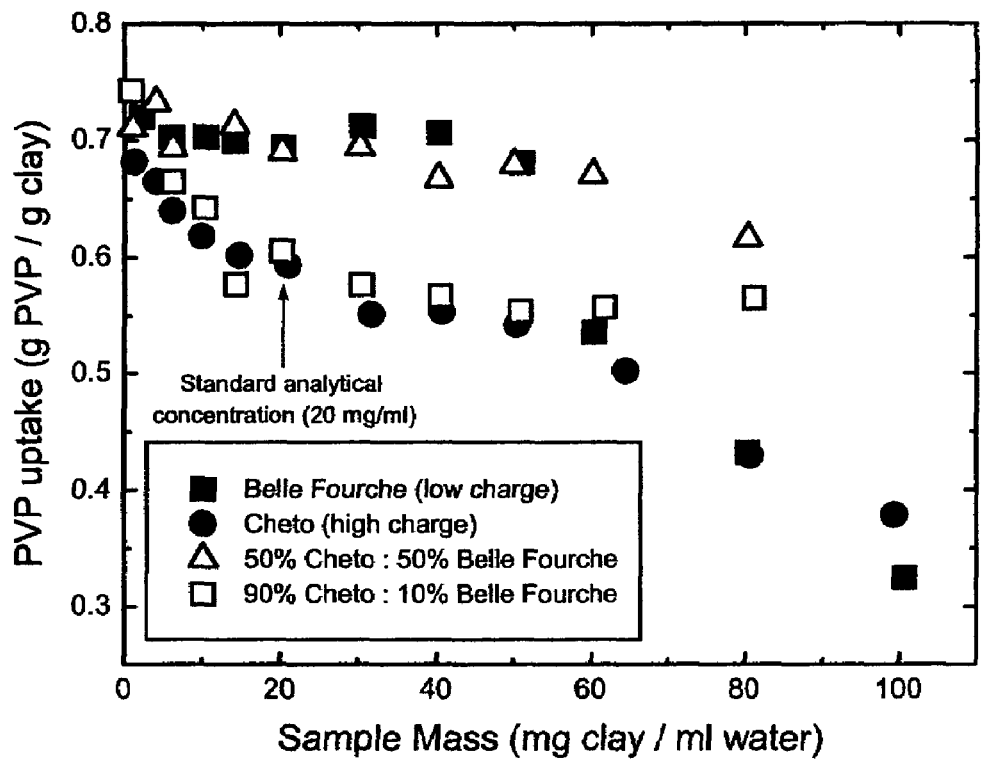
FIG. 5 is a graphical representation of the effect of solid to solution ratio on PVP uptake.

One issue in designing a technique using PVP to measure smectite surface areas was the effect of the suspension density (g clay/mL water). The higher the solid to solution ratio, the greater the sensitivity of the technique, since a greater proportion of the PVP in solution is sorbed. As seen in the graphical representation of the effect of solid to solution ratio on PVP uptake in FIG. 5, low charge smectites, such as the Belle Fourche and Wyoming bentonites, had very little dependence on the suspension density. However, high charge smectites such as the Cheto and Kinney displayed a strong dependence on suspension density. The cause of this solid/solution ratio effect remains unclear, but is generally consistent with the higher charge smectites having a greater tendency to form aggregates in solution before the PVP is added. However, the PVP sorption of the high charge smectites is very reproducible, and is not strongly dependent on the time the solution sits between ultrasonic dispersion and addition of the PVP. This suggests that only a subpopulation of particles tend to aggregate quickly, rather than a highly time dependent phenomenon.

The abundance of low-charge versus high-charge smectites in most natural environments is not known, since this is a quantity which can only be determined accurately on pure samples, usually from bentonites or hydrothermal veins. These environments, although economically important, are not representative of most natural sediments. Differences in dispersion caused by charge density differences could lead to considerable uncertainty in the surface area determination of unknown samples by PVP sorption. However, it was found that mixtures of low and high charge smectites do not vary their sorption properties in a simple linear mixing (see FIG. 5). The addition of 50% low charge smectite to 50% high charge smectite results in PVP sorption behavior nearly identical to that of a pure low charge sample. Thus, the solution density should not be a significant effect for samples <50% high-charge smectite. This assumption can be tested by measuring two different sample masses, which should yield the same PVP sorption density, and this is the recommended procedure for samples of unknown composition. However, the mechanism causing this behavior of high-charge smectites remains unclear.

TABLE 1

PVP uptake measurement of various minerals.

| Sample | Mineral | PVP-55K uptake (g/g) | Surface Area ($m^2/g$) | PVP Surface Area ($m^2/g$) | PVP-55K uptake ($mg/m^2$) |
|---|---|---|---|---|---|
| Belle Fourche | montmorillonite | 0.72[a] | 725[b] | 725 | 0.99 |
| Belle Fourche (Ca-sat.) | montmorillonite | 0.44 | 725[b] | 443 | 0.61 |
| Wyoming "B" | montmorillonite | 0.71 | 725[b] | 715 | 0.98 |
| Wyoming B (Ca-sat.) | montmorillonite | 0.46 | 725[b] | 463 | 0.63 |
| Kinney | high charge smectite | 0.71 | 752[b] | 715 | 0.98 |
| SAz-1 (Cheto) | high charge smectite | 0.71 | 717[b] | 715 | 0.99 |
| SAz-1 (Cheto) (Ca-sat.) | high charge smectite | 0.33 | 717[b] | 332 | 0.46 |
| Hectorite | Li-smectite | 0.72 | 725[c] | 725 | 0.99 |
| Camp Berteau | montmorillonite | 0.71 | 725[c] | 715 | 0.98 |
| Red Hill | montmorillonite | 0.72 | 725[c] | 725 | 0.99 |
| Bates Park Montana | montmorillonite | 0.64 | 725[c] | 644 | 0.88 |
| Glen Silver Pit, Idaho | montmorillonite | 0.50 | 725[c] | 503 | 0.69 |
| Fe smectite | nontronite | 0.64 | 654[d] | 644 | 0.98 |
| Saute Loupe | nontronite | 0.65 | 654[d] | 655 | 0.99 |
| Amargosa | sepiolite | 0.34 | | 342 | |
| IMV | sepiolite | 0.23 | | 232 | |
| Arkansas Rectorite | | 0.36 | 363[c] | 363 | 0.99 |
| Slovakia K-rectorite | | 0.35 | 363[c] | 352 | 0.96 |
| Wyoming "C" | montmorillonite | 0.71 | 725[c] | 715 | 0.98 |
| Dry Branch | kaolinite | 0.012 | 14.0[e] | 12 | 0.86 |
| Kga 1 | kaolinite | 0.0089 | 10.0[e] | 9 | 0.89 |
| Kga 2 | kaolinite | 0.018 | 22.6[e] | 18 | 0.82 |
| Libby | Vermiculite | 0.005 | | small | |
| SG4 | illite | 0.034 | 35[f] | 34 | 0.97 |
| RM30 (Na sat) | illite | 0.071 | 63[f] | 71 | 1.13 |
| RM30 (Ca sat) | illite | 0.073 | 63[f] | 74 | 1.16 |
| Marblehead | illite | 0.105 | 117[f] | 106 | 0.90 |
| Fithian, Illinois | illite | 0.074 | 176[f] | 75 | 0.42 or 8%[h] |
| 3M3 | illite | 0.51 | 201[g] | 514 | 61% smectite[h] |
| IM5 | illite | 0.31 | 148[g] | 312 | 29% smectite[h] |
| activated carbon | reagent | 0.11 | 883[e] | 111 | 0.12 |
| Florida peat | humic standard | −0.017 | | | |
| $Fe_2O_3$ | hematite | 0.0103 | 10.5[e] | 10 | 0.98 |
| fumed $SiO_2$ | amorphous | 0.13 | 280[e] | 131 | 0.46 |
| $Al(OH)_3$ | amorphous | 0.0014 | | ~0 | |
| $Al(OH)_3$ | synthetic gibbsite | −0.003 | 0.09[e] | ~0 | |
| $\gamma$-$Al_2O_3$ | reagent | 0.0016 | 175[e] | ~0 | |
| ZnO | reagent | 0.0025 | 3.83[e] | | 0.65? |

[a]The uptake of PVP-10K, 40K and 360K are approximately 0.61, 0.68 and 0.76 g/g, respectively.
[b]Calculated based on measured chemistry, the molar volume of muscovite and 1 nm thick crystals.
[c]Estimated surface area (see text).
[d]Calculated assuming a composition of $NaFe_4Si_{7.34}Al_{0.66}O_{20}(OH)_4$, an ideal nontronite.
[e]$N_2$ BET surface area.
[f]Computed from illite particle thickness distributions based on MudMaster XRD measurements.
[g]Surface areas measured by MudMaster (XRD). However, these samples are very thin illites which probably contain single unit cell smectite particles which are not detected by XRD.
[h]The % smectite is computed based on measured PVP uptake and the MudMaster surface area for the illite component.

D. XRD Evidence for the Thickness of Sorbed PVP

Figure 6A:
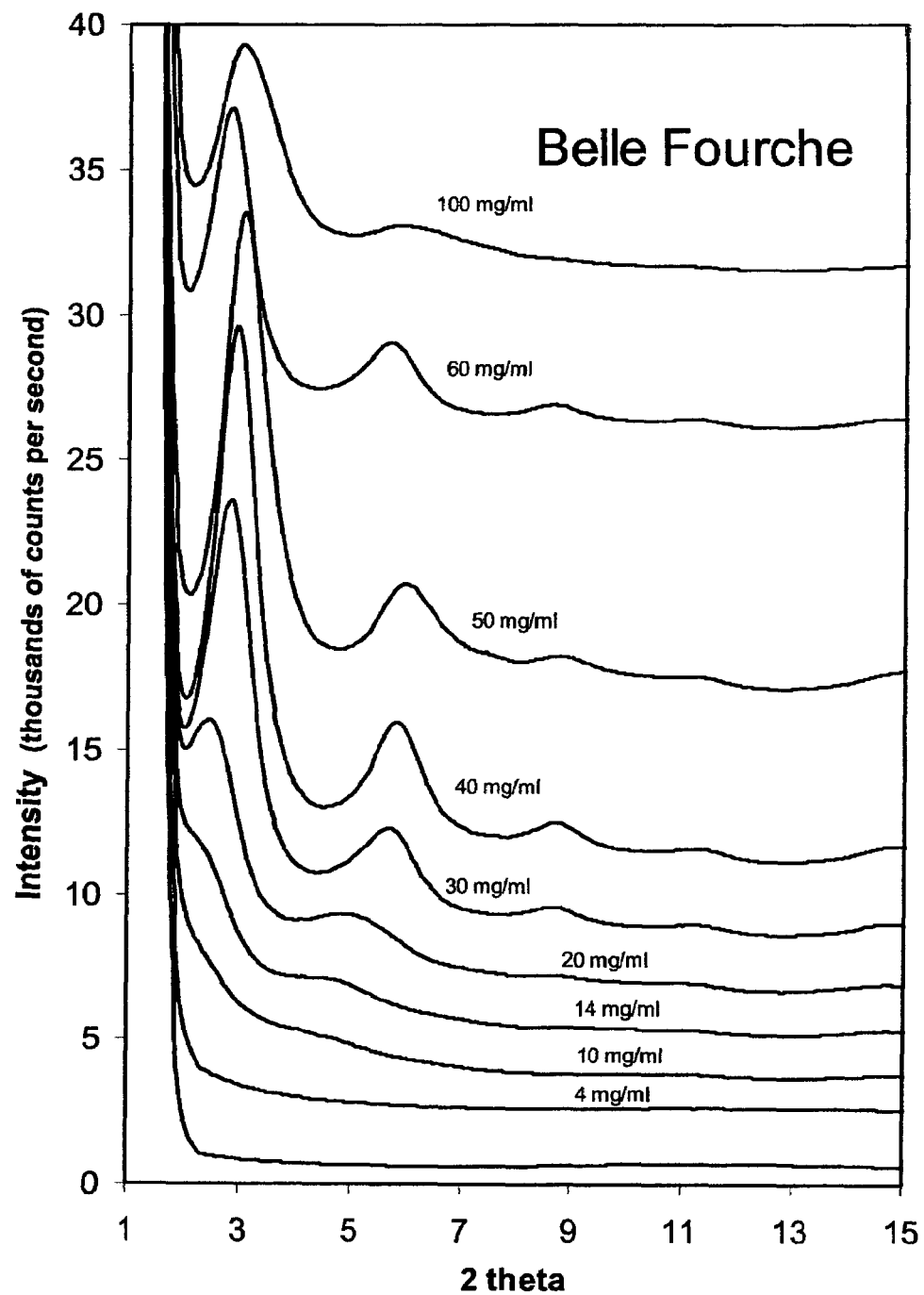
FIG. 6(a) shows XRD patterns of Belle Fourche low charge montmorillonite, at different solid to solution ratios.
Figure 6B:
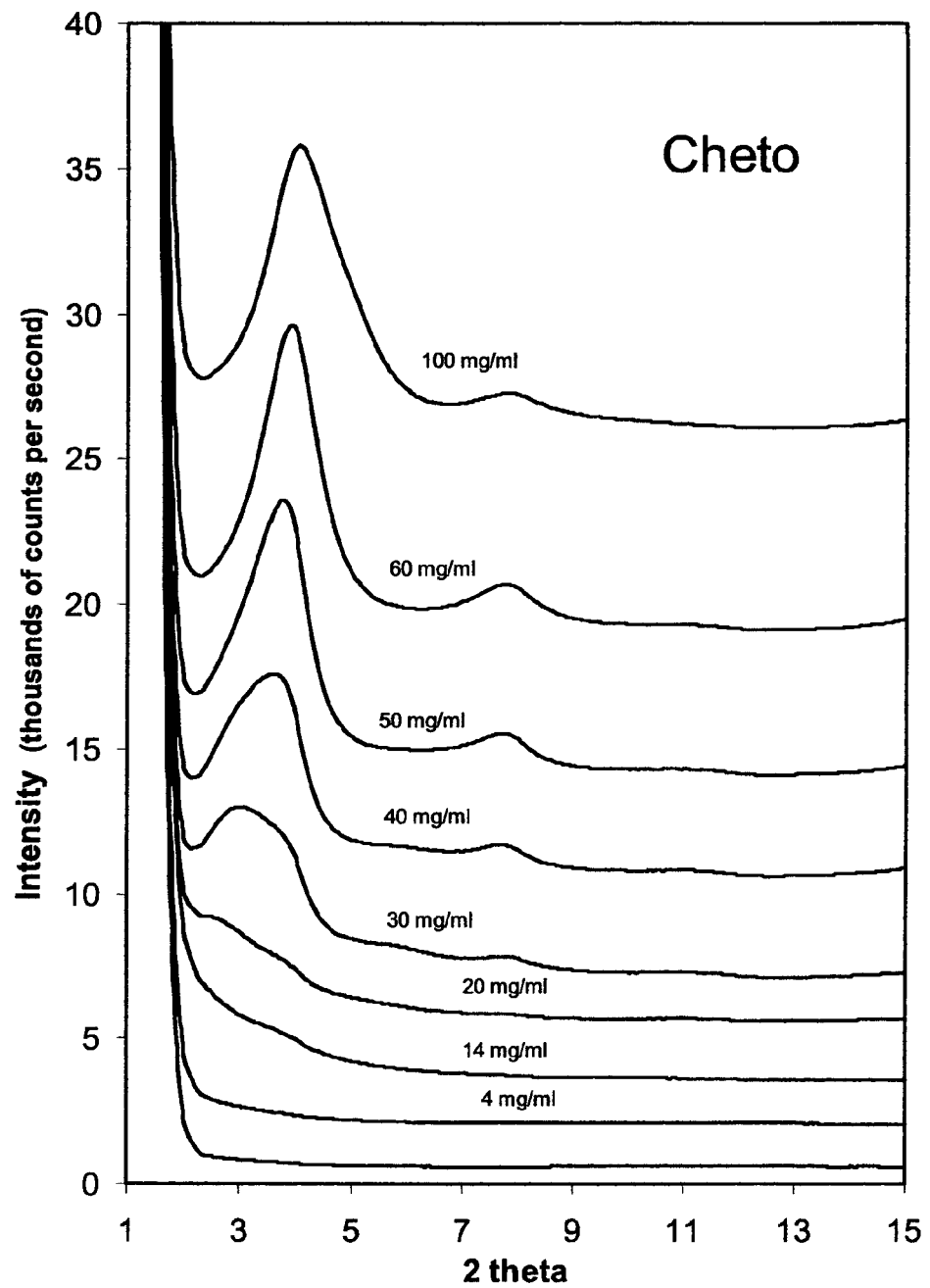
FIG. 6(b) shows XRD patterns of Cheto high charge montmorillonite, at different solid to solution ratios.

XRD patterns for smectite solutions with different solid-to-solution ratios reveals some insight into the difference in behavior of low-charge and high-charge smectites, as seen in FIGS. 6(s) and 6(b) showing XRD patterns of (a) Belle Fourche low charge montmorillonite in FIGS. 6(a) and (b) Cheto high charge montmorillonite in FIG. 6(b), at different solid to solution ratios. However, FIGS. 6(a) and 6(b) reflect smectite orientations after evaporation and not in solution. All smectites dispersed in PVP solutions with a low solid-to-solution ratio (SSR) had no XRD (001) diffraction peaks. XRD patterns show only the smectite structure factor and weak and broad reflections from the PVP matrix. This is consistent with the observations of Eberl et al. (1998), previously identified, for a dilute suspension of Kinney smectite in PVP. The lack of diffraction peaks in dilute solutions indicates that the smectites are dispersed as single unit cell crystals with enough excess PVP between the particles after evaporation to completely eliminate interparticle diffraction. However, as the solid-to-solution ratio increases, the low-charge and high-charge smectites display different behaviors. For example, the Belle Fourche has no XRD peaks until a SSR of approximately 14 mg/ml, at which point a peak appears at approximately 34.5 Å along with its higher orders. At low angles such as this, the Lorentz polarization factor (Lp) has a significant effect on peak shapes and positions. All d-spacings were determined after Lp removal, although FIGS. 6(a) and 6(b) show the uncorrected XRD patterns. The peak at 34.5 Å increases in intensity with increasing SSR until approximately 50 mg/ml, beyond which the intensity continues to increase, but the peak position also moves to higher angles, reaching 27 Å at a SSR of 100 mg/ml, and the higher angle reflections become less rational.

In contrast to the Belle Fourche sample, the Cheto high-charge smectite has a very weak peak at approximately 23.5 Å at the lowest SSR of 1 mg/ml, which is detectable only at a greatly expanded scale from FIG. 6(b). The 23.5 Å peak increases in intensity with increasing SSR, and shifts to slightly higher angles, approaching 22 Å at a SSR of 100 mg/ml. The Kinney, also a high charge smectite, has a behavior intermediate between the Belle Fourche and Cheto (not shown in FIGS. 6(a) and 6(b)). At a low SSR, the Kinney smectite has a weak peak at approximately 34.5 Å, which increases in intensity as the SSR increases. At an SSR of 30 mg/ml the peak begins to shift to a progressively lower d-spacing, finally reaching approximately 23 Å at a SSR of 100 mg/ml. The multiples of the high-angle peaks initially become more irrational as the peak position moves away from 34.5 Å, and then become more rational again as the peak position approaches 23 Å.

Figure 7:
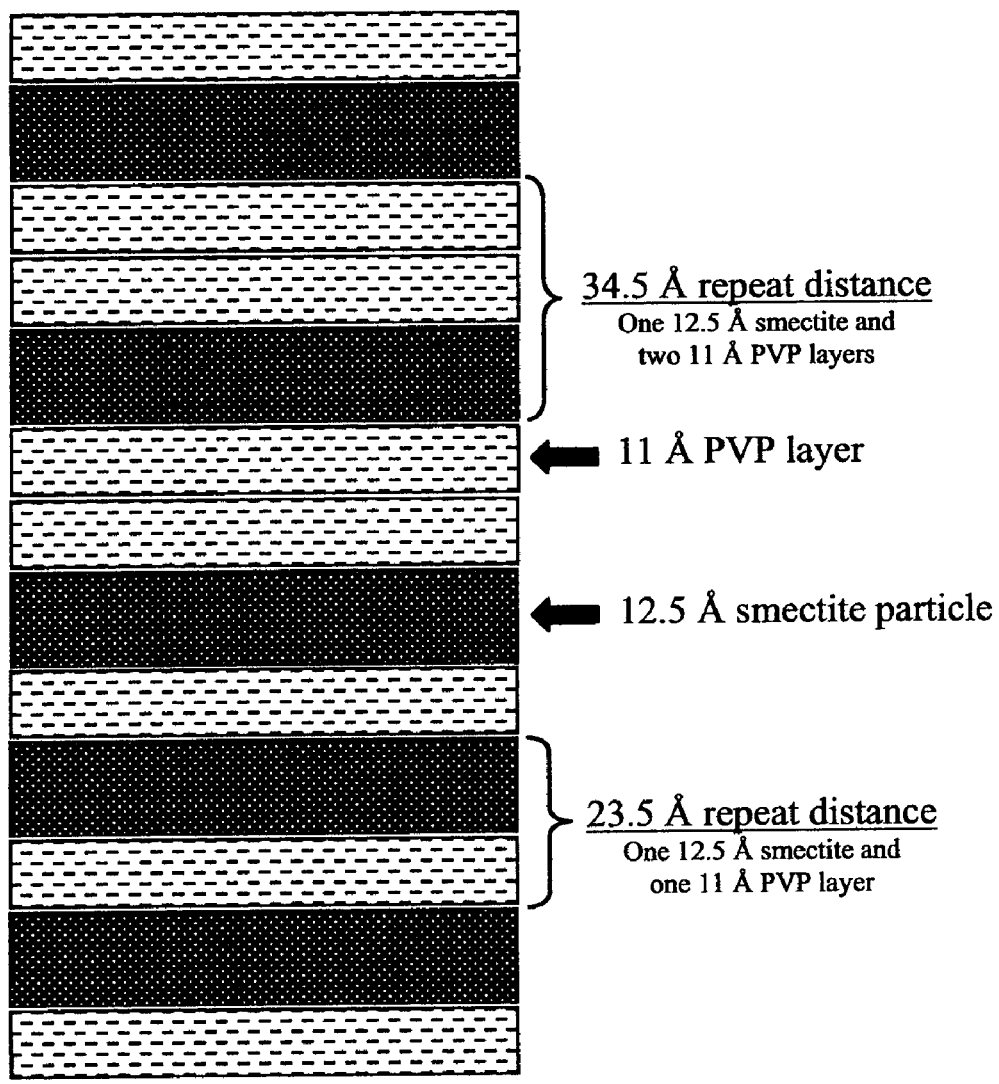
FIG. 7 represents proposed structure for generating the 34.5 Å and 23.5 Å repeat distances observed in XRD patterns.

These XRD observations can be explained by a simple structure, with stacking of 12.5 Å smectite crystals (10 Å 2:1 silicate layer +2.5 Å due to hydration of the surface) with either one or two 11 Å thick PVP interlayers. The conceptual model, shown in FIG. 7, represents proposed structure for generating the 34.5 Å and 23.5 Å repeat distances observed in XRD patterns. At low SSR values, all the clays have a tightly bound 11 Å layer of PVP sorbed on their surfaces, but there is sufficient unbound PVP in solution to widely separate the clay crystals, yielding no XRD peak when dried. In the case of Belle Fourche, as the SSR increases and the clay particles become more closely packed, some crystals begin to align, creating interparticle diffraction with a 34.5 Å periodicity. Basically, as the number of particles increases and the amount of PVP in solution stays nearly constant, there is less PVP between each particle to disrupt interparticle diffraction. Since the amount of PVP sorption on each surface remains at 11 Å, these interparticle associations, if present in solution, would not affect the amount of PVP taken up from solution. This is consistent with the observation that the PVP sorption on Belle Fourche is not changed by SSR's below approximately 50 mg/ml (see FIG. 5). Comparisons may be made to the computed thickness of the sorbed PVP layer based on the observed uptake from solution (see FIG. 3). Assuming the smectite particles have a density of 2.5 g/cm$^3$ and a thickness of 12.5 Å, and the PVP layer has a density of 1.1 g/cm$^3$, the PVP surface layer is calculated from the PVP uptake of 0.73 g/g to have a thickness of 10.2 Å, in good agreement with the XRD data of 11 Å.

As the SSR of the Belle Fourche increases above approximately 50 mg/ml, this starts to randomly interstratify only one layer of PVP between smectite layers. This produces a spacing of 23.5 Å, which causes the shift of the 34.5 Å peak to smaller apparent spacings with a loss in rationality of the multiple d-spacings. This is typical randomly interstratified mixed-layer XRD behavior (see e.g., Moore, D. M.; Reynolds, R. C., Jr (1989) X-ray diffraction and the identification and analysis of clay minerals. Oxford Univ. Press, New York, pp. 332). Formation of 23.5 Å aggregates in solution would produce a reduced PVP uptake, since two surfaces share one PVP layer, with each surface being effectively only 50% covered. This is consistent with the reduced PVP uptake by Belle Fourche at SSR's above approximately 50 mg/mL (see FIG. 5).

In contrast to the Belle Fourche, the Cheto starts with a few 23.5 Å aggregates even at an SSR of 1 mg/mL, and the number of aggregates increases quickly with increasing SSR. This would be consistent with the formation of 23.5 Å aggregates in solution, which explains why the uptake of PVP on the Cheto appears strongly dependent on the SSR even at low SSR values. The shift of peak positions to <23.5 Å at the highest SSR-s SSR's may indicate the interstratification of 12.5 Å interlayers with no intercalated PVP at the highest clay concentrations. The Kinney at first forms 34.5 Å aggregates, but progressively moves toward 23.5 Å at higher SSR-s SSR's much more quickly than the Belle Fourche, with a randomly interstratified structure during the transition.

Thus, the uptake of PVP from solution as a function of SSR (see FIG. 5) is consistent with the XRD evidence, and it appears the XRD patterns reflect aggregates of clay crystals which formed in solution. Based on the relative rates of PVP sorption versus particle aggregation, it is believed that the clay particles are dispersed in solution prior to the addition of PVP, as evidenced by all smectites being nearly completely dispersed at low SSR's. Once the PVP solution is added, the PVP sorbs to all the clay surfaces before the particles aggregate. If this occurs, an 11 Å A PVP layer forms on all the surfaces, and the PVP uptake from solution is independent of the SSR. However, if the smectite particles associate before completion of the PVP sorption, then some clay particles may end up sharing a PVP layer with an adjacent particle, forming the 23.5 Å structure. As the SSR of the suspension increases, the mean distance between particles in solution decreases, increasing the likelihood of particles associating before PVP sorption is complete, and favoring the formation of the 23.5 Å structure. It is assumed that high-charge smectites have a greater propensity to aggregate than low-charge smectites, and would be more sensitive to the SSR.

E. Illite and Vermiculite

Natural sediments usually contain a complex mixture of clay minerals, and so it is important to investigate the effects of a broader spectrum of minerals on PVP uptake. Illites are the other clay mineral with a high surface area present in many soils and sediments. Illites have a structure very similar to smectites, except that the fundamental particles are 2 unit cells thick, and interior (001) interfaces are fixed by potassium ions that cannot be cation exchanged or expanded by ultrasonic dispersion, ethylene glycol or EGME. The exterior (001) surfaces of the illites should behave in a similar manner as smectites, and the exterior unit cells of illites are thought to have a chemistry and fixed charge that are similar to low-charge smectites (see Srodon, J., Morgan, D. J., Eslinger, E. V., Eberl, D. D., and Karlinger, M. R., 1986, Chemistry of illite/smectite and end-member illite: Clays and Minerals, v. 34, p. 268-378.). Sorption of PVP on a range of different illites (see Table 1) is consistent with this conceptual model. When normalized to illite surface area determined by MudMaster (Eberl et al., 1996, previously identified, the disclosure of which is hereby incorporated by reference), illites have the same PVP sorption density and behavior as low-charge smectites.

The specific surface areas ($m^2/g$) of illites can at most be 50% that of smectite (assuming all the illite crystals are 2 unit cells thick, e.g., a rectorite), and the surface area decreases rapidly as the illite particles increase in thickness. PVP sorption on two different rectorites, in which most of the particles are about 2 nm thick, is shown in Table 1, and is about half the value of smectites on g/g basis, as would be expected if the particles are 2 unit cells thick. When illite particles reach a mean thickness of about 12 nm, they have a specific surface area approximately 8.3% that of smectites. Thus, if illite is abundant it may contribute significantly to the amount of PVP sorbed by a sample, and in samples with a low abundance of smectite mixed with a large amount of thin illites, illite may dominate the PVP sorption. Therefore, it is necessary to correct PVP-based measurements of smectite abundance for illite in samples where significant illite is present, as described below.

The behavior of vermiculites presents a middle ground between the behavior of illite and smectite. The interlayer cations in vermiculites are exchangeable, but are not swollen by ethylene glycol, and vermiculite is not dispersed into "fundamental" particles. Rather, vermiculites maintain "large" crystals with a low external surface area, but with the interlayers accessible for cation exchange. It appears that PVP does not enter the vermiculite interlayers (see Table 1), and that vermiculites are not a significant source of PVP sorption.

F. Oxides

Figures 8A, 8B:
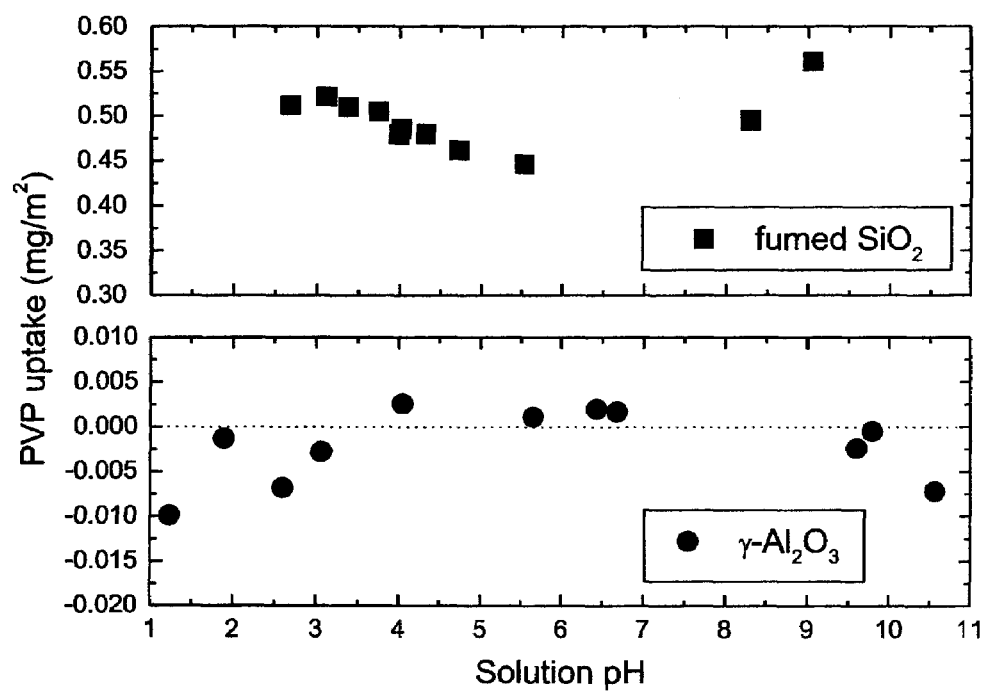
FIG. 8(a) is a graphical representation of PVP uptake by $SiO_2$ as a function of solution pH.
FIG. 8(b) is a graphical representation of PVP uptake by $\gamma$-$Al_2O_3$ as a function of solution pH.

Graphical representations of PVP uptake by (a) $SiO_2$ and (b) $\gamma$-$Al_2O_3$ as a function of solution pH are shown in FIGS. 8(a) and 8(b) respectively. The sorption of PVP on amorphous (fumed) silica, shown in FIG. 8(a), has a similar sorption density as smectite and illite surfaces (see Table 1). These data are consistent with the PVP sorption data of Thibaut, et al. (Thibaut, A., Misselyn-Bauduin, A. M., Broze, G. and Jerome, R. 2000) Sorption of poly(vinylpyrrolidone)/Surfactant(s) mixtures at the silica/water interface. Langmuir, 16:9841-9849.) and Cohen et al. (Cohen Stuart, M. A., Fleer, G. J., and Scheutjens, J. M. H. M. (1984) Displacement of polymers. II. Experiment. Determination of segmental sorption energy of poly(vinylpyrrolidone) on silica. J. Colloid and Interface Sci., 97:526-535.). Quartz was not measured, because grinding to a sufficiently fine grain size to detect PVP sorption produced abundant amorphous material. Presumably, quartz acts in manner similarly to amorphous silica, since the local surface chemistry of amorphous $SiO_2$ and quartz are similar, and PVP sorption appears so insensitive to the detailed surface structure. In natural samples, quartz may be high in abundance but with low surface area, and even highly pitted quartz will contribute insignificantly to the surface area in comparison to smectite.

In contrast to amorphous silica, $\gamma$-$Al_2O_3$ sorbed no PVP, shown in FIG. 8(b). The point of zero charge (PZC) of $\gamma$-$Al_2O_3$ is near pH 8.5 (see e.g., Haung, C. P. and Stumm, W. (1973) Specific sorption of cations on hydrous $\gamma$-$Al_2O_3$. J. Colloid Interface Sci., 22:231-259). Changing the solution pH on either side of the PZC to create positively and negatively charged $\gamma$-$Al_2O_3$ surfaces had no effect on the lack of PVP sorption. The apparent increasingly negative values for $\gamma$-$Al_2O_3$ PVP uptake at low and high pH are thought to be an artifact, the result of $Al_2O_3$ dissolution, which increases the mass of solids in solution. Minimal PVP sorption to the alumina surface has also been reported by Otsuka and Esumi (1994) and Esumi et al. (2000). Similar to $\gamma$-$Al_2O_3$, gibbsite and amorphous $Al(OH)_3$ showed no PVP sorption, and it appears that aluminum oxyhydroxides are not a significant contribution to PVP uptake. However, hematite ($Fe_2O_3$) showed PVP uptake equivalent to the silicates on a per surface area basis (see Table 1).

G. Kaolinite

Figure 9:
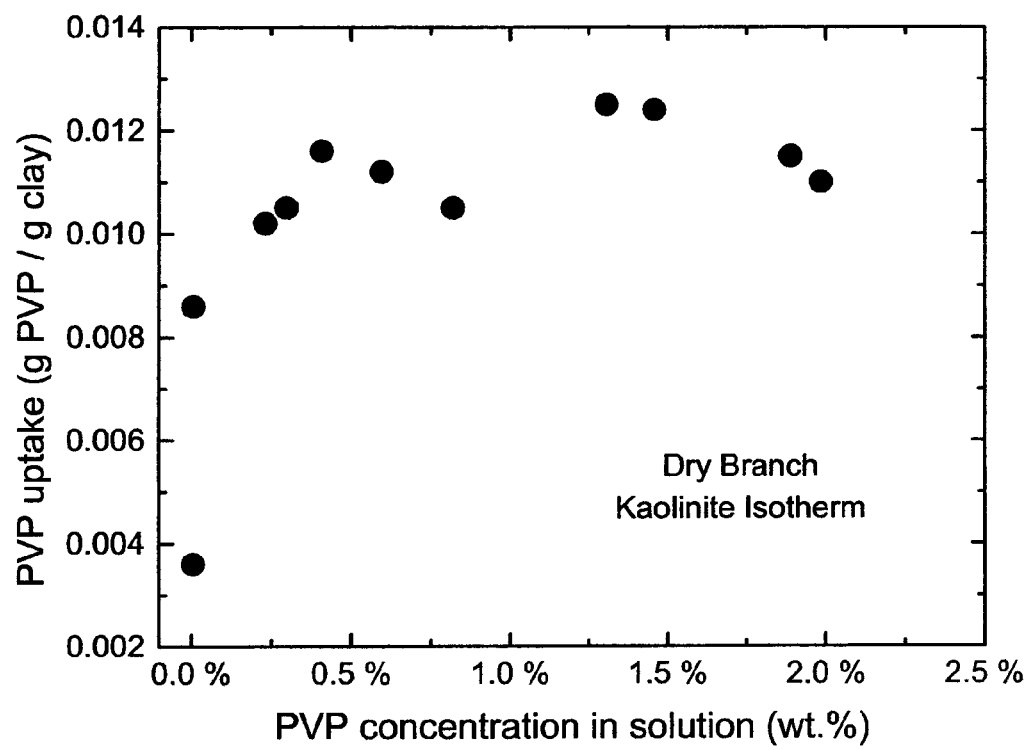
FIG. 9 is a graphical representation of PVP sorption isotherm for Dry Branch kaolinite.
Figure 10:
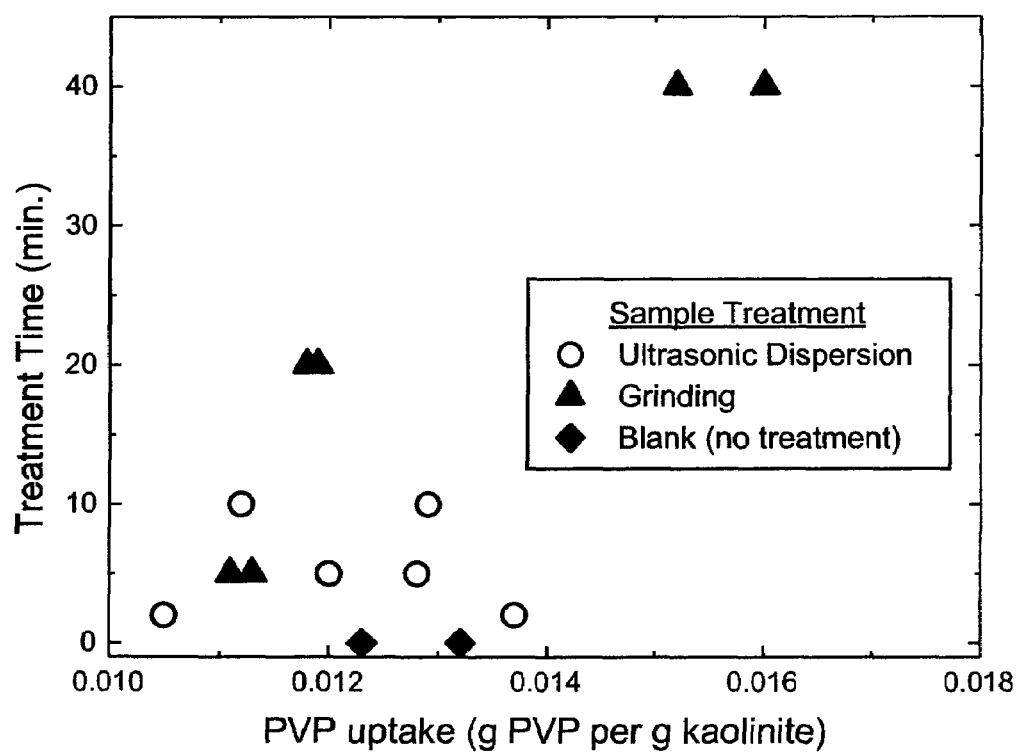
FIG. 10 is a graphical representation of the effect of ultrasonic dispersion and grinding pretreatments on the amount of PVP uptake on Dry Branch kaolinite; and, FIG. 11(a) shows a graphical representation of measured surface area for mixtures having variable amounts of smectite with the remaining portion of the sample being a single additional phase, as a function of predicted surface area.

Kaolinite presents a somewhat different situation from smectite and illite. For any kaolinite crystal, one surface should be an octahedral Al—OH surface and the other side a tetrahedral Si—O—Si surface. Based on the oxide analysis, PVP would be expected to sorb on the tetrahedral side and not on the octahedral side, producing a PVP sorption per unit surface area (g $PVP/m^2$) that is one half that of smectites and illite. As seen in FIG. 9, a graphical representation of PVP sorption isotherm for Dry Branch kaolinite is depicted. Although kaolinite uptake of PVP, shown in FIG. 9, is near the detection limit for this technique, but it appears that they sorb PVP in a similar manner and at the same surface density as smectites and other minerals, in contradiction with our expectation. Bonding between kaolinite layers is weak, and previous AFM observations have shown that vigorous ultrasonic treatment can generate some 7 Å thick kaolinite crystallites (Blum and Eberl, 1992, previously identified). Qualitatively, these single-layer crystals appeared to be a very small fraction of the total sample, but concern that the experimental procedure could be increasing the amount of kaolinite surface area present in the sample. If ultrasonic dispersion doubled the kaolinite surface area, then the apparent sorption of PVP on both surfaces of the kaolinite based on the BET surface area could be explained. FIG. 10 is a graphical representation of the effect of ultrasonic dispersion and grinding pretreatments on the amount of PVP uptake on Dry Branch kaolinite. FIG. 10 shows that increasing the duration of ultrasonic treatment of the kaolinite had no impact on the amount of PVP sorbed, and that this procedure does not distort the results. However, grinding the kaolinite in a McCrone mill (a variety of vibrating rod mill) does systematically increase the PVP uptake by the sample, presumably by grinding of the kaolinite to a finer grain size, and thus, increasing the surface area.

H. Organic Matter

One consideration for natural samples is the effect of organic matter on PVP sorption. One end-member for organic carbon is activated carbon, which has a very high and reactive surface area (883 $m^2/g$). PVP did sorb on activated carbon with an average density of 0.12 mg/m2, significant but much lower than the value of ~1 mg/m2 for silicates. The most likely explanation is that PVP sorbed on to activated carbon at about the same density as on silicates. However, a large portion of the activated carbon surface area is internal, as is obvious from its silt size particles which have a surface area actually higher than smectites. Apparently, many of these pores are small enough that PVP-55K cannot access the interior. However, the internal porosity would be accessed by $N_2$, and thus, the sorption density based on $N_2$ BET surface areas appears low.

Consequently, organic carbon has the potential to uptake PVP. However, shales and sediments are rarely more than a few wt. % organic carbon, and natural organic material typically has surface areas that are orders of magnitude smaller than activated carbon. For example, a Florida (Pahokee) peat (an International Humic Substances Society source material), is highly reactive and high surface area natural organic material, but has a small apparently negative uptake of PVP. The dissolved organic matter imparted a dark yellow-brown color to the PVP solution, consistent with an increase in dissolved organic matter (DOC) in solution, and the apparent negative PVP uptake. This indicates that even with a thoughly water-washed sample, the PVP in solution solubilized (presumably by complexation) more organic matter than PVP was sorbed on the organic surfaces. It was observed that some organic-rich shales also impart a dark brown color to the PVP solution, indicating the solubilization of organic matter. It appears that the major caveat for organic rich samples may not be the uptake of PVP by the organics, but the potential solubilzation of DOC by the PVP measurement procedure. It may, therefore, be advantageous to wash organic rich samples with an organic solvent or also destroy reactive organic matter with peroxide or another oxidant before the PVP analysis of organic rich samples. An advantage of PVP uptake by organic carbon may be that organics sorbed to the clay surfaces will not greatly affect the measured surface areas of the clays, and should not interfere with smectite abundance measurements.

I. The Nature of PVP Sorption

Preferably, the present invention addresses PVP sorption on silicates, based on the observations as previously described. The insensitivity of the absolute mass of PVP sorbed on chain length indicates the PVP chains are lying parallel to the silicate surface, so that the area covered per polymer is approximately proportional to the polymer length. The large area covered by each PVP polymer, coupled with the apparent lack of sensitivity of PVP sorption to the details of surface chemistry, layer charge or solution pH, suggest the interaction between adjacent PVP chains is a major factor in the formation of the surface layer. However, no indications were seen of the addition of more than an approximately 11 Å thick layer of PVP to the surface, suggesting the surface also plays an important role in the formation of the PVP layer, and this is not a surface precipitation type process. The XRD peaks at 23.5 and 34.5 Å (see FIGS. 6(a) and 6(b)) also suggest the sorbed layer is relatively uniform in thickness, since a variability in the thickness of the PVP layer between particles would not produce a coherent XRD signal. The observations are all consistent with the sorption of a monolayer of PVP chains on the surface, although there is no direct evidence as to the organization of PVP within the sorbed layer. The reason why the Si—OH surface of fumed silica sorbs PVP but the Al—OH surface of gibbsite (or γ-$Al_2O_3$) do not sorb PVP is not known.

J. Accuracy of PVP Uptake as a Measure of Surface Area

In light of the difficulties in constraining the accuracy of a PVP uptake measurement as a measure of surface area, described herein, Table 1 presents data from a wide range of materials. However, the only parameter directly describing PVP sorption is grams of PVP sorbed per gram of sample. The repeatability of measurement is generally (as detailed herein) very good, and almost always better than ±5% for smectite-rich samples. However, this quantity is difficult to evaluate independently. In looking at the sorption per unit surface area, values are easily compared, generally within a range that incorporate some degree of error in the surface area determinations. The results of different smectites may also be compared. Theoretically, the only difference the specific surface area of the different smectites is the difference in density resulting from variations in the chemical composition of the unit cell. In general, the smectites shown in Table 1 are in good agreement, clustering around 0.72 g/g. However, the purity of any smectite sample which has not been extensively characterized is always suspect, and "impurities" may explain PVP uptake numbers below 0.72 g/g. For example, the Glen Silver Pit smectite in Table 1 has a PVP uptake of 0.50 g/g, which may result from contamination with a small amount of amorphous material, illite, or another silicate. One constant aspect of the smectite data in Table 1 is that no samples yielded a PVP uptake significantly above 0.72 g/g.

The determination of illite surface areas are dependent upon the MudMaster analysis. The use of MudMaster as a technique for determining illite surface areas appears to be valid (Eberl et al., 1998, previously described), with precise accuracy difficult to ascertain. Illite sample purity also introduces an uncertainty for many illite samples. Finally, the use of $N_2$ surface areas for the non-clays for comparison with PVP surface areas is useful, but as suggested by the measurements of activated carbon, the surface area accessible to $N_2$ with a MW of 28 and PVP with a MW of 55,000 are not necessarily equivalent, especially if there is considerable internal microporosity. With these conditions, relatively consistent result of about 0.99 mg of PVP 55K sorbed per $m^2$ of surface area on a range of smectites, illites, silica and other materials are seen (Table 1), indicating that PVP uptake can be accurately used to quantify silicate mineral surface area.

K. Quantitative measurement of smectite abundance

To quantify the amount of smectite in a complex mixture, it is necessary to know how much PVP has been sorbed by other phases, such as illite, kaolinite, quartz and feldspars. However, non-clay silicate minerals rarely make up a significant portion of the <2 μm fraction of natural samples and their surface areas are very low. Therefore non-clays contribute very little to the total sample surface area. For example, in a sample which is 1 wt. % smectite and 99 wt. % 2 μm diameter spheres (ñ=2.8 g/$cm^3$), the smectite would account for 88% of the total surface area. If the spheres are 5 μm, 1 wt % smectite would account for >95% of the surface area. Even in fine-grained natural samples, the non-clays will rarely contribute significantly to the total surface area if smectite is present, and can simply be ignored. An exception may be ferrihydrite, which may occur in abundance near active redox interfaces, such as outflows from sulfide rich tailings piles. Ferrihydrite has a highly variable surface area, initially up to several hundred m2/g, but decreasing rapidly with recrystallization over a period of days to weeks. The presence of ferrihydrite could therefore complicate any PVP analysis, and may require removal by selective dissolution before a meaningful PVP uptake measurements can be performed.

Illite and kaolinite generally have surface areas only a fraction of smectites, but they may still contribute a significant proportion of the surface area and PVP uptake if smectite is present in only small proportion. Thus, the surface area attributable to smectite in a sample can be calculated as:

$$SA^*_{sample} = (SA^*_{kaolinite})(M_{kaolinite}) + (SA^*_{illite})(M_{illite}) + (SA^*_{smectite})(M_{smectite}) \quad (eq.\ 2)$$

where M is mass fraction of the mineral in the sample, and SA* is the specific surface area. We must then solve eq. 2 for $M_{smectite}$.

$SA_{total}$ is determined experimentally as:

$$SA^*_{sample}\ [m^2/g] = \text{mass of PVP uptake } [g/g]/0.99\ [g/m^2] \quad (eq.\ 3)$$

The SA* of smectite was calculated earlier from the molar volume and formula weight to be approximately 725 $m^2/g$. The wt % kaolinite in the sample can be determined using the quantitative XRD techniques (see Srodoń et al. (2001), previously identified, the disclosure of which is hereby incorporated by reference). The specific surface area of the kaolinite are unknown and must be estimated. The surface areas of kaolinites do not vary as greatly as illites; and are generally near 25 $m^2/g$ for poorly crystallized kaolinites, with well ordered kaolinites slightly lower, as low as 10 $m^2/g$. Thus, $SA_{total}$ is approximately 30 times more sensitive to the abundance of smectite than kaolinite. In most cases the total kaolinite correction is small, and the uncertainties in the kaolinite surface areas are not significant.

$SA^*_{illite}$ can be calculated from the crystal size distribution obtained from the (001) XRD peak shape using MudMaster measurements, as described earlier. The wt. % of illite in the sample can not be determined using the quantitative XRD techniques of Srödon et al. (2001), but the wt. % of illite plus smectite ($M_{ill+smec}$) can be determined (from the (060) reflection of a randomly oriented sample). Thus, substitution of $[M_{ill+smec} - M_{smectite}]$ for $[M_{illite}]$ in equation 2 is appropriate, and solve for $M_{smectite}$.

$$M_{smectite} = SA^*_{total} - (SA^*_{kaolinite})(M_{kaolinite}) - (SA^*_{illite})(M_{illite+smectite})/755 - SA^*_{illite} \quad (eq.\ 4)$$

Thus, eq. 4 can be used to determine the mass of smectite in a sample, even in the presence of significant amounts of illite and kaolinite.

Figure 11A:
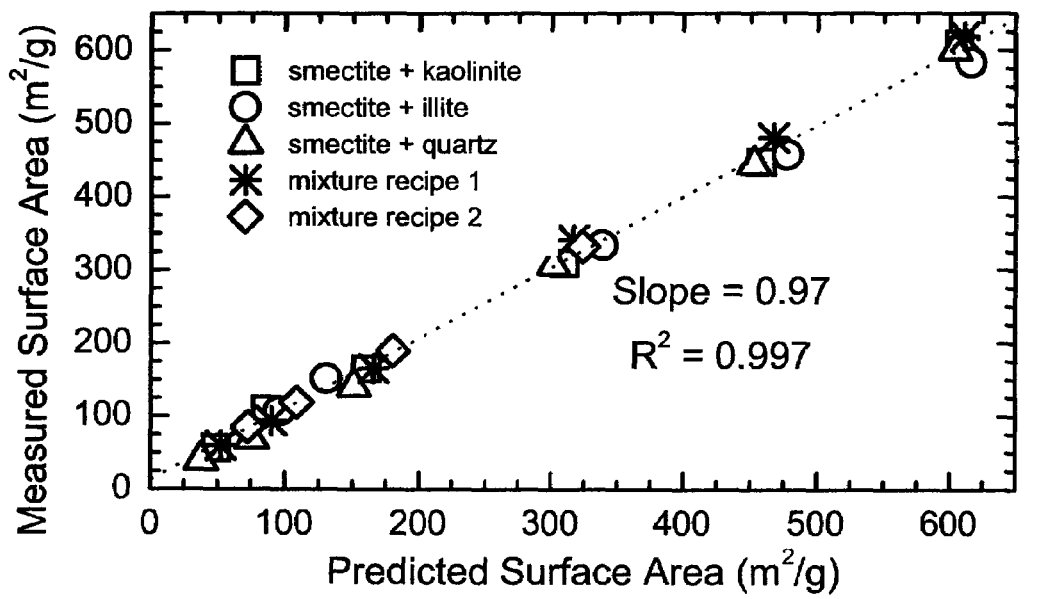
FIG. 11(b) shows a graphical representation of measured smectite for mixtures having variable amounts of smectite with the remaining portion of the sample being a single additional phase, as a function of smectite in sample.
Figure 11B:
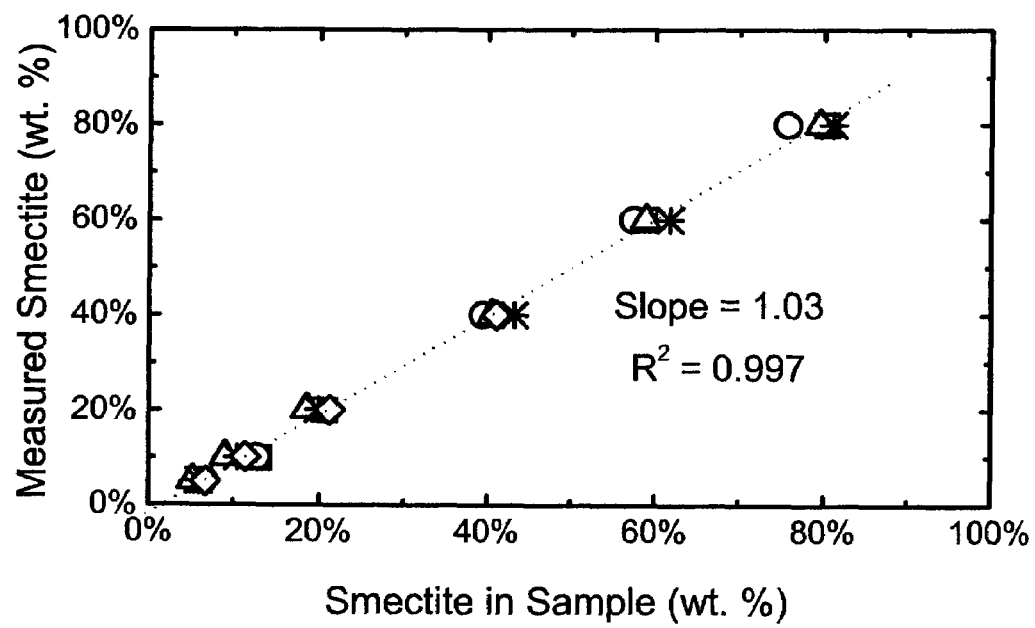

Analyses of several artificial mixtures are shown in shows FIGS. 11(a) and 11(b). FIGS. 11(a) and 11(b) show graphical representations of the first three mixtures are variable amounts of smectite with the remaining portion of the sample a single additional phase. Mixtures were made by combining measured amounts of Belle Fourche smectite (montmorillonite, SA=725 $m^2/g$), Dry Branch kaolinite (SA=14.0 $m^2/g$ by BET), RM30 illite (mean particle thickness of 11.6 nm and surface area of 63 $m^2/g$ by MudMaster) and quartz (ground in a shatter box; assumed SA<<1 $m^2/g$). The mixtures were divided into 5 series, with smectite varying between 5% and 80% in each series. The specific surface area of each mixture can be calculated by using the surface areas of the components in the proper proportions. The measured PVP uptake and equation 3 to calculate a sample specific surface area, and equation 4 to determine the smectite content of the sample are then used. As would be expected, the non-smectite components had the largest relative impact on the specific surface area when samples had low smectite concentrations and/or high illite content. Sample series 1 contains variable amounts of smectite with the remainder divided equally between kaolinite and illite. Sample series 2 contains smectite plus 20% each kaolinite and illite with the remainder quartz, except 80% smectite, which has 10% each of kaolinite and illite, with (a) the surface area measured by PVP uptake versus the surface area predicted from the composition of the sample and the independently determined surface areas of the components and (b) the composition of the smectite measured in the samples by PVP uptake and the amount of smectite mass added to the sample. Both FIG. 11(a) and FIG. 11(b) show good linear correlations between measured and predicted values, with a slope of approximately 1. The components all appear to act independently in suspension, with no interaction or aggregation which impacts the PVP uptake. This indicates both the validity and sensitivity of the approach outlined in equations 1 and 2 which uses PVP uptake by complex mixtures to determine the smectite content of samples. However, purified component was used which can be easily dispersed. Cements in natural samples, might affect the ability to disperse clays, and possibly impact the PVP uptake.

L. Applications of the PVP Technique

Because smectites have a significant influence on the properties of many natural and synthetic materials, both as a major phase and a minor contaminant, there are a large number of potential problems for which the ability to quantitatively measure smectite abundance would be helpful. Several applications include, for example without limitation, the characterization of petroleum reservoirs and cap rocks, and reaction paths within sedimentary basins; prediction of the geotechnical properties of soils and rocks, particularly the detection of swelling potential in soils; the characterization of bentonites and other clays for application in ceramics, paper, drilling fluids and liners; determining the provenance of sediments in fluvial and lacustrine systems and other like applications.

EXAMPLE 1

For surface area determination by PVP, the sample is typically Na (or Li) saturated with 1 M NaCl to assure complete dispersion of smectite particles, and then washed to remove all soluble salts which might interfere with measurement of PVP concentration by weight. Dialysis bags with a molecular weight pore size of 10K are effective for both removing residual NaCl and any other low molecular weight soluble material which might be present in the sample, while retaining all the clay particles. The procedure is detailed as:

A 15 mL centrifuge tube with lid is weighed, and then approximately 50 mg of dry smectitic clay sample (or other material with an equivalent surface area of approximately 40 $m^2$) is weighed into the centrifuge tube. Into the 15 mL centrifuge tube, about 5 mL of water is added, and the smectitic clay sample is thoroughly dispersed with an ultrasonic probe. The tube is then weighed, and approximately 2 mL of 10% PVP 55K is added, after which the tube is reweighed. The smectitic clay sample is then shaken overnight, and centrifuged until the solids are completely separated from the solution, which generally occurs after approximately 4 hours at 10,000 rpm. A sample vial is weighed with the lid, solution is decanted from the centrifuge tube into the vial, closed and weighed. The beaker is then dried at 851 C overnight, capped immediately after being removed from the oven, and reweighed when cooled.

The mass of PVP sorbed on the sample is then calculated as the difference between the mass of PVP added to the centrifuge tube and the mass of PVP remaining in solution after the sorption reaction, as calculated from the measured PVP concentration, and the original amount of solution in tube, as determined by mass. All masses are determined within the experimental error range of the equipment, which is preferably less than or equal to $\forall 0.0001$ g.

The uptake of polyvinylpyrrolidone (PVP) gives an accurate measure of the surface area of silicate minerals exposed while dispersed in solution. The sorbed PVP layer is approximately 11 Å thick, and corresponds to approximately 0.99 g 55K PVP per $m^2$ of surface area. Sodium saturated smectites can be readily dispersed as single unit cell crystals, and they tend to dominate sample surface areas. Therefore, PVP uptake (0.73 g PVP per g smectite) can be used to quantify the abundance of smectitic minerals in a sample. Quantitative XRD techniques can be used to further refine the measurement of smectite abundance by correcting the sample for sample illite and kaolinite surface areas.

The foregoing summary, description, examples and drawings of the invention are not intended to be limiting, but are only exemplary of the inventive features which are defined in the claims.

What is claimed is:

1. A method of quantitatively determining the surface area and mass of smectite in a sample, comprising the steps of:
   selecting a solution;
   dispersing a sample comprising smectite in the solution;
   adding a quantitative mass of polyvinylpyrrolidone in the solution, wherein the polyvinylpyrrolidone deposits on the surface of the smectite;
   removing at least a portion of the solution having the added polyvinylpyrrolidone that has not deposited on the dispersed smectite;
   determining the mass of the polyvinylpyrrolidone deposited on the surface area of the smectite from the transfer of polyvinylpyrrolidone from the solution to the surface of the smectite;
   calculating the smectite area of the smectite from the determined mass of the polyvinylpyrrolidone deposited on the surface area of the smectite; and
   determining the mass of smectite in the sample from the calculated surface area.

2. The method of claim 1, wherein the step of determining the mass of the polyvinylpyrrolidone deposited on the surface area of the sample comprises quantifying the mass of the added polyvinylpyrrolidone, that has not deposited on the dispersed sample, from the removed at least a portion of the solution.

3. The method of claim 1, wherein the step of determining the mass of the polyvinylpyrrolidone deposited on the surface area of the sample comprises determining the loss of polyvinylpyrrolidone from the solution from the quantified mass of added polyvinylpyrrolidone.

4. The method of claim 3, wherein the step of determining the mass of the polyvinylpyrrolidone deposited on the surface area of the sample comprises determining the mass of the polyvinylpyrrolidone deposited on the surface area of the sample from the determined loss of polyvinylpyrrolidone from the solution.

5. The method of claim 1, wherein the sample comprises a fine grained material.

6. The method of claim 5, wherein the fine grained material comprises a clay.

7. The method of claim 1, wherein the solution is selected from the group consisting of water, one or more organic solvents and combinations thereof.

8. The method of claim 7, wherein the solution comprises water.

9. The method of claim 1, wherein the step of dispersing the sample in the solution includes saturating the sample's exchange sites with sodium or lithium ions.

10. The method of claim 9, further comprising the step of removing excess sodium or lithium salt from the sample prior to adding polyvinylpyrrolidone in the solution.

11. The method of claim 1, wherein the step of dispersing the sample in the solution includes a means of dispersal selected from the group consisting of stirring, shaking, ultrasonic agitation, and combinations thereof.

12. The method of claim 1, further comprising the step of concentrating the sample with deposited polyvinylpyrrolidone prior to the step of removing the at least a portion of the solution.

13. The method of claim 12, wherein the step of concentrating the sample includes a concentrating means selected from the group consisting of centrifugation, flocculation, dialysis and combinations thereof.

14. The method of claim 13, wherein the step of concentrating the sample comprises centrifugation.

15. The method of claim 1, wherein the polyvinylpyrrolidone adsorbs on the smectite independent of smectite layer charge, organic content of the sample, and presence of iron oxides.

* * * * *